United States Patent
Nomura et al.

(10) Patent No.: US 7,504,162 B2
(45) Date of Patent: Mar. 17, 2009

(54) CARBAZOLE DERIVATIVE, ORGANIC SEMICONDUCTOR ELEMENT, LIGHT EMITTING ELEMENT, AND ELECTRONIC DEVICE

(75) Inventors: Ryoji Nomura, Kanagawa (JP); Satoshi Seo, Kanagawa (JP); Harue Nakashima, Kanagawa (JP)

(73) Assignee: Semiconductor Energy Laboratory Co., Ltd., Kanagawa-Ken (JP)

( * ) Notice: Subject to any disclaimer, the term of this patent is extended or adjusted under 35 U.S.C. 154(b) by 291 days.

(21) Appl. No.: 10/839,123

(22) Filed: May 6, 2004

(65) Prior Publication Data

US 2005/0031899 A1    Feb. 10, 2005

(30) Foreign Application Priority Data

May 16, 2003  (JP) .............................. 2003-139432

(51) Int. Cl.
*C07D 209/82* (2006.01)
*C07D 417/00* (2006.01)
*C07D 411/00* (2006.01)
*C07D 413/00* (2006.01)
*H01L 51/50* (2006.01)

(52) U.S. Cl. ................. 428/690; 428/917; 313/504; 548/440; 257/40

(58) Field of Classification Search ............ 428/690, 428/917; 313/504; 257/40; 548/440
See application file for complete search history.

(56) References Cited

U.S. PATENT DOCUMENTS

2003/0205696 A1 *  11/2003  Thoms et al. .......... 252/301.16

FOREIGN PATENT DOCUMENTS

JP            08003547 A  *  1/1996

(Continued)

OTHER PUBLICATIONS

Kundu et al., Adv. Func. Mater. (2003), vol. 13, No. 6, June, p. 445-452.*

(Continued)

*Primary Examiner*—Dawn Garrett
(74) *Attorney, Agent, or Firm*—Nixon Peabody LLP; Jeffrey L. Costellia

(57) ABSTRACT

The problem of the present invention is to provide a carbazole derivative which has an excellent heat resistance and can be formed into a film without crystallization. Also, a problem is to produce an organic semiconductor element, a light emitting element and an electronic device by employing the carbazole derivative. For the purpose, a novel carbazole derivative represented by following general formula (1) is provided:

(1)

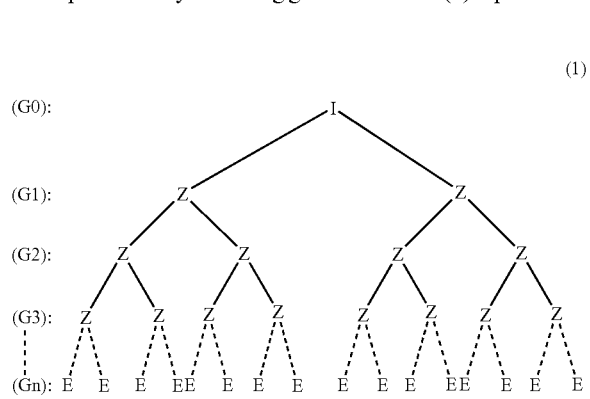

(in the formula, I represents a core carbazole ($G_0$) illustrated by general formula (2), Z represents an internally branched carbazole ($G_1$ to $G_{n-1}$) illustrated by general formula (3), E represents an end carbazole ($G_n$) illustrated by general formula (4), n represents an integer showing generation number of dendrimer, $X_1$ represents hydrogen, halogen, a cynano group, an alkyl group, an aryl group, a heterocyclic residue or the like, $X_2$ and $X_3$ in ($G_{(n-m)-1}$) (provided, n-m≧1) make a covalent bond with $X_4$ in ($G_{(n-m)}$), and each of $R_1$ to $R_8$ represents independently hydrogen, halogen, a cynano group, an alkyl group, a dialkylamino group, a diarylamino group, a heterocyclic residue or the like).

I:

Z:

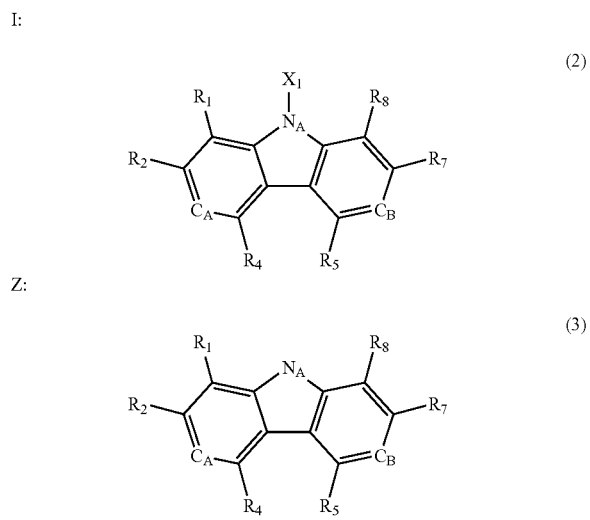

E:

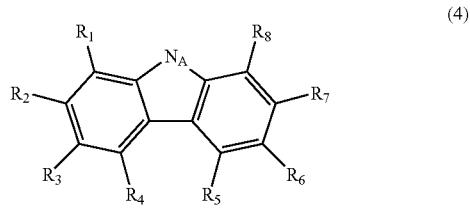

(4)

22 Claims, 18 Drawing Sheets

FOREIGN PATENT DOCUMENTS

| JP | 10-226785 | | 8/1998 |
|---|---|---|---|
| JP | 2001-244077 | | 9/2001 |
| JP | 2001-257076 | | 9/2001 |
| JP | 2002-100480 | | 4/2002 |
| JP | 2003133075 A | * | 5/2003 |
| JP | 2003-267976 | | 9/2003 |
| JP | 2003-317966 | | 11/2003 |
| JP | 2004-18787 | | 1/2004 |
| WO | WO-03/079736 A1 | | 9/2003 |

OTHER PUBLICATIONS

Kimoto et al., Chemistry Letters, vol. 32, No. 8, (2003), p. 674-675.*
Kimoto et al., Macromolecules, (2004), vol. 37, p. 5531-5537.*
JPO computer-generated English translation of JP 2004-018787 published Jan. 22, 2004.*
Grigalevičius et al., "*Hole-Transporting Molecular Glasses Based on Carbazole and Diphenylamine Moieties*", Materials Chemistry and Physics, vol. 72, pp. 395-400 (2001).
Grigalevičius et al., "*Synthesis and Properties of Poly(3,9-Carbazole) and Low-Molar-Mass Glass-Forming Carbazole Compounds*", Polymer, vol. 43, pp. 2603-2608 (2002).
Grigalevičius et al., "*Photoconductive Molecular Glasses Consisting of Twin Molecules*", Journal of Photochemistry and Photobiology A: Chemistry, vol. 154, 99. 161-167 (2003).
Hameurlaine et al., "*Synthesis of Soluble Oligocarbazole Derivatives*", Tetrahedron Letters, vol. 44, pp. 957-959 (2003).
McClenaghan et al., "*Ruthenium(II) Dendrimers Containing Carbazole-Based Chromophores as Branches*", Journal of the American Chemical Society, vol. 125, pp. 5356-5365 (2003).
Zhang et al., "*Carbazole-Based Hole-Transporting Materials for Electroluminescent Devices*", Synthetic Metals, vol. 137, pp. 1111-1112 (2003).
Written Opinion (Application No. PCT/JP2004/006435; PCT 7135) dated Jul. 27, 2004.
English Translation of Written Opinion for Application No. PCT/JP2004/006435; PCT 7135, dated Jul. 27, 2004.

* cited by examiner

CARBAZOLE DERIVATIVE, ORGANIC SEMICONDUCTOR ELEMENT, LIGHT EMITTING ELEMENT, AND ELECTRONIC DEVICE

TECHNICAL FIELD

The present invention relates to a carbazole derivative being a dendrimer compound, an organic semiconductor element, a light emitting element and an electronic device employing the carbazole derivative.

BACKGROUND ART

An organic compound, compared with an inorganic compound, is rich in variety of material system and has a possibility to synthesize materials having various functions by a suitable molecular design. In addition, it has characteristics such that formed things thereof such as a film are rich in flexibility and, further, processability is good by forming a high molecular weight. Due to these advantages, recently, photonics and electronics employing functional organic material have grabbed attention.

For example, a solar cell and a light emitting element (also referred to as an organic electroluminescent device) can be mentioned as examples of a photoelectronics device employing an organic semiconductor material as a functional organic material. These are devices taking advantage of electric properties (carrier transport properties) and optical properties (light absorption or light emission) of the organic semiconductor material. Among them, in particular, a light emitting element has made remarkable development.

The light emitting element is constituted by sandwiching a layer containing a light emitting material between a pair of electrodes (anode and cathode). The light emitting mechanism thereof is said that a hole injected from an anode and an electron injected from a cathode when a voltage is applied between both electrodes recombine in a layer containing a light emitting material to recombine at an emission center in the layer containing the light emitting material to form a molecular exciton, and that the molecular exition emits energy upon returning to the ground state to emit light. As for the exited state, the singlet excitation and triplet excitation are known, and light emission is thought to be possible via either excited state.

The layer containing a light emitting material may be a single layer structure of only a light emitting layer composed of a light emittable material, or may be formed by laminating a hole injecting layer, a hole transporting layer, a hole blocking layer, an electron transporting layer, an electron injecting layer and the like composed of plural functional materials, in addition to the light emitting layer. In the light emitting layer, it is possible to change arbitrarily hue of the emitted light by doping a guest material into a host material. In addition, some combinations of a host material and a guest material have the potential to improve brightness and lifetime of the light emitting.

As for the material for use in a layer containing the light emitting material, many materials having various structures and functions are employed. Among them, CBP (4,4-di(N-carbazole)biphenyl), PVK (polyvinyl carbazole) and the like are known as a material (carbazole derivative) having a carbazole skeleton with an excellent photoconductivity, and are used aboundingly still at the present day.

CBP, which is a low molecular weight material, is formed into a film mainly by an evaporation method and is aboundingly employed as a host material having hole transporting properties in the light emitting layer (for example, refer to Patent Document 1).

(Patent Document 1) JP-A-2001-244077

However, although the material has the characteristic of a high thermal property value (good heat resistance), it has a demerit such that maintenance of an amorphous state is difficult upon forming a film to crystallize easily.

On the other hand, PVK, which is a high molecular weight material, is formed into a film mainly by a wet process such as a coating method (including spin coating method) and a ink jet method, and are employed aboundingly as a host material in the light emitting layer similar to CBP (for example, refer to Patent Document 2).

(Patent Document 2) JP-A-2001-257076

When used as a host material in the light emitting layer, a high molecular weight material has the characteristic such that it excels in brightness properties (maximum brightness is several tens of thousands $cd/m^2$) compared with a low molecular weight material. However, it has demerits such that it has a bad heat resistance and low reliability, as well as can be formed into a film only by limited methods.

Accordingly, both of the low molecular weight material and the high molecular weight material having a carbazole skeleton have aforementioned demerits respectively, and development of a material overcoming these demerits is desired in order to improve further element properties of the light emitting element.

Thus, the present invention aims to provide a carbazole derivative which has an excellent heat resistance and is difficult to crystallize when formed into a film. In addition, the invention aims to accomplish extending lifetime of an organic semiconductor element and a light emitting element by producing the organic semiconductor element and the light emitting element while employing the carbazole derivative.

DISCLOSURE OF THE INVENTION

Constitution of the invention is to provide a novel carbazole derivative. Note that, the carbazole derivative according to the invention has a structure represented by general formula (1) below.

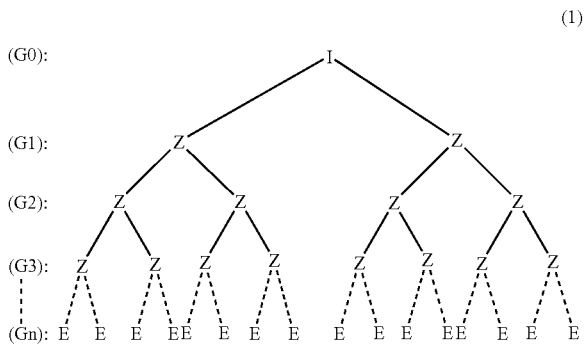

(in the formula, I represents a core carbazole ($G_0$) illustrated by general formula (2), Z represents an internally branched carbazole ($G_1$ to $G_{n-1}$) illustrated general formula (3), E represents an end carbazole ($G_n$) illustrated by general formula (4), n represents an integer showing generation number of dendrimer, $X_1$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue, $X_2$ and $X_3$ in ($G_{(n-m)-1}$) (provided, n-m≧1) make a covalent bond with $X_4$ in ($G_{(n-m)}$), and each of $R_1$ to $R_8$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10) or a substituted or unsubstituted heterocyclic residue.)

I:

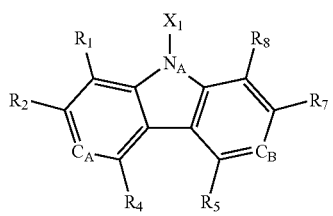
(2)

Z:

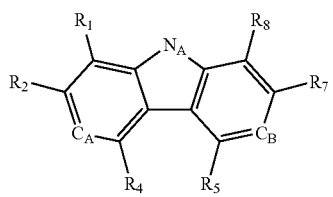
(3)

E:

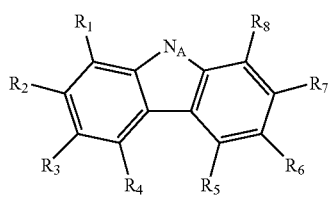
(4)

The carbazole derivative according to the invention has a structure represented by general formula (5).

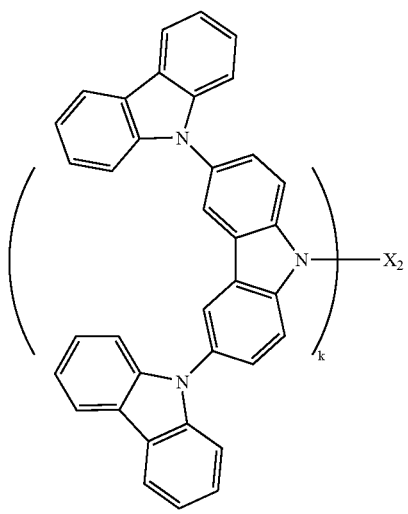
(5)

(in the formula, $1<k<8$ and $X_2$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue.)

Further, the carbazole derivative according to the invention has a structure represented by general formula (6).

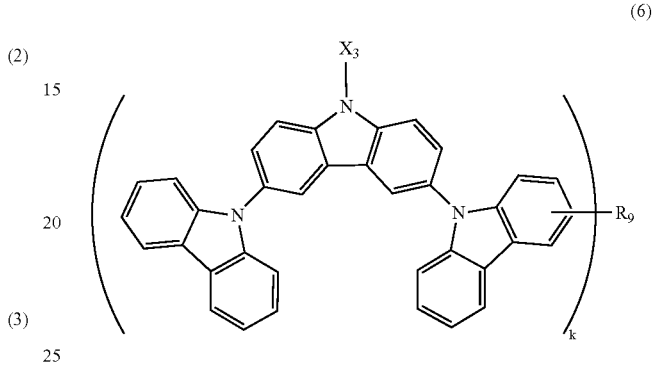
(6)

(in the formula, $1<k<8$, each of $R_9$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10), a substituted or unsubstituted aryl group or a substituted or unsubstituted heterocyclic residue, and $X_3$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue.)

Furthermore, the carbazole derivative according to the invention has a structure represented by general formula (7).

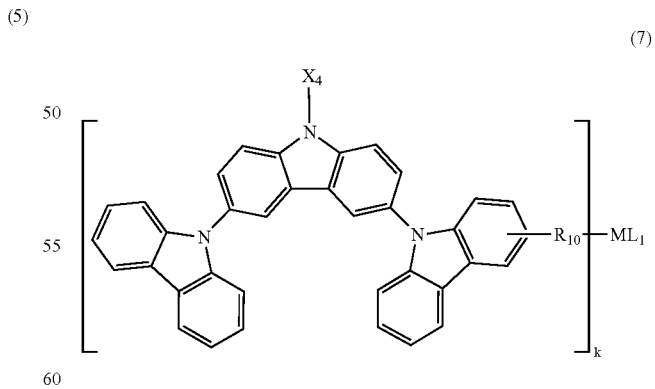
(7)

(in the formula, $1<k<8$, $0<1<8$, each of $R_{10}$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10), a substituted or unsubstituted aryl group or a substituted or unsubstituted heterocyclic residue, M represents a metal ion of zero to hexavalent, L represents an aryl group, a dialkylphosphino group or a diarylphosphino group, and $X_4$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue.)

In addition, among carbazole derivatives according to the invention, $R_1$ to $R_8$ in the aforementioned general formulae ((2) to (4)), and $R_9$ in the aforementioned general formula (6) are characterized by being any one of heterocyclic residues represented by structural formula (8).

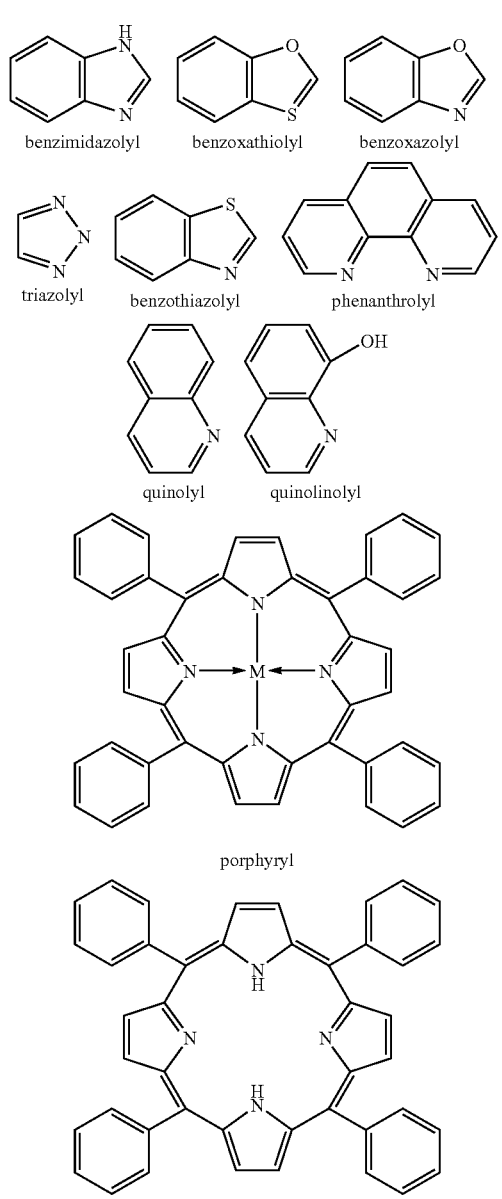

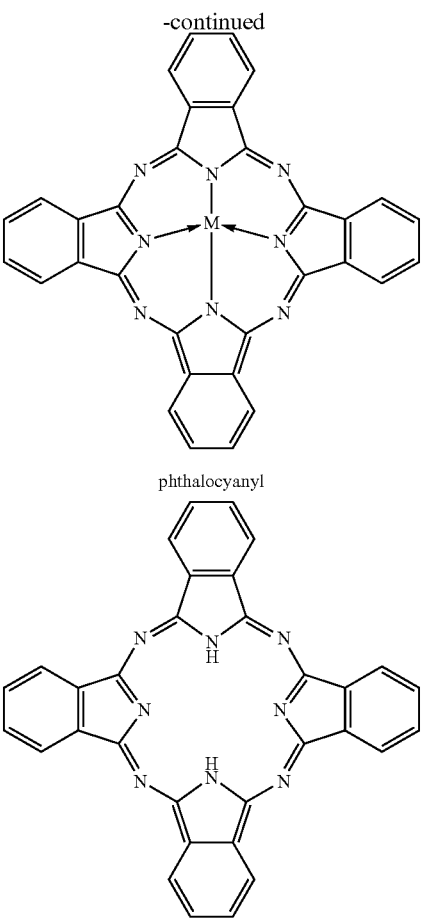

Further, in the invention, constitution of an organic semiconductor element characterized by employing the aforementioned carbazole derivative as an active layer of the organic semiconductor element is intended to be included.

Furthermore, in the invention, constitution of a light emitting element characterized by having a light emitting layer containing the aforementioned carbazole derivative is intended to be included. Note that, the carbazole derivative according to the invention has the characteristic of a wide energy gap, therefore it may be used as a host material to form a light emitting layer with another guest material.

In the aforementioned constitution, the carbazole derivative according to the invention is particularly preferred in the case where a phosphorescent material requiring a host material with a wide energy gap is employed as a guest material. In addition, the carbazole derivative according to the invention can be also employed as a guest material.

Since the carbazole derivative according to the invention is a material excellent in hole transport properties, the aforementioned carbazole derivative can be employed as a hole transportable material for a light emitting element.

BEST MODE FOR CARRYING OUT THE INVENTION

Embodiment Mode 1

Figure 1:
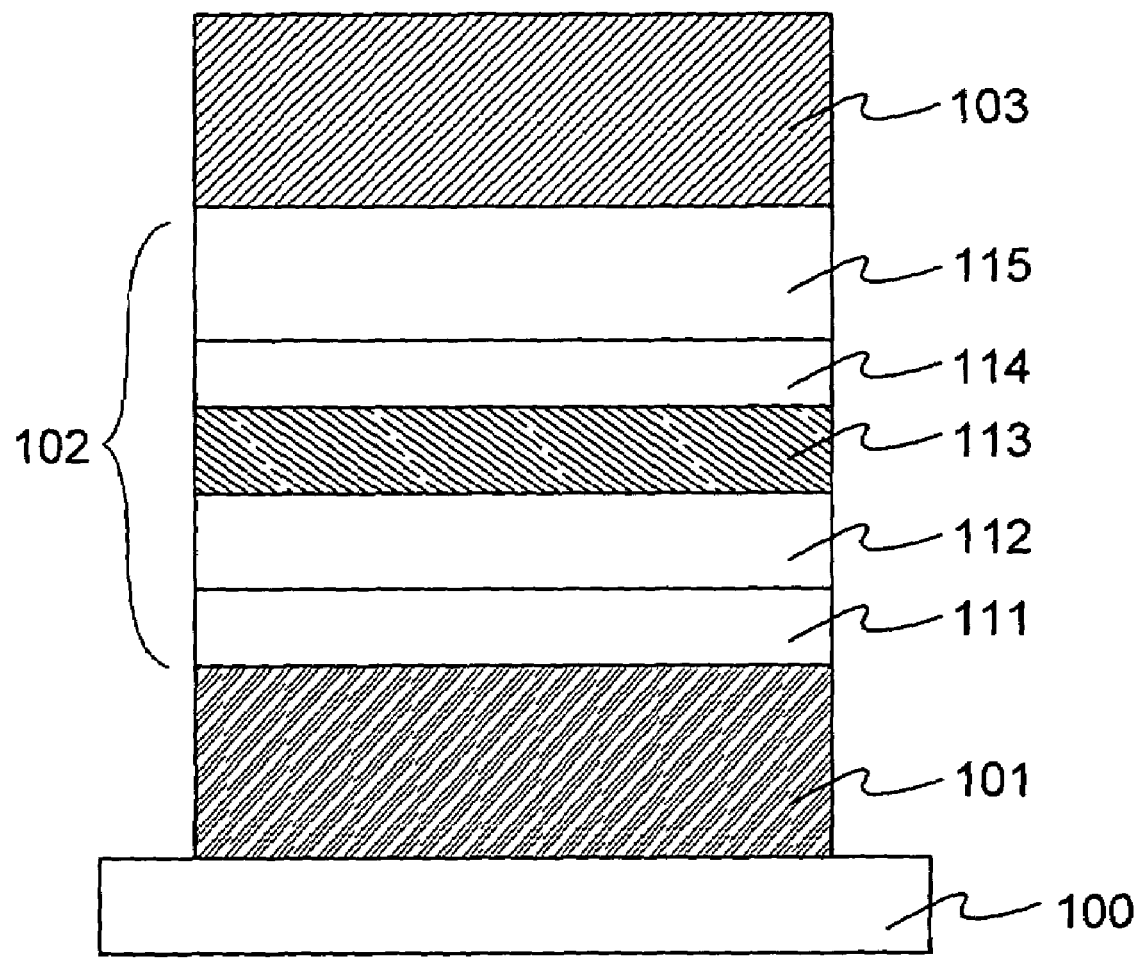
FIG. 1 is a drawing for explaining an element structure of a light emitting element according to the invention.

The carbazole derivatives in the invention are those having structures represented by the aforementioned general formulae (1) to (7).

For example, as the carbazole derivative of a first generation ($G_1$) in the general formula (1), the structure represented by structural formula (9), for example, can be mentioned. Specifically, it has the construction in which $N_A$ of the end carbazole (E) represented by the general formula (4) makes covalent bonds with $C_A$ and $C_B$ of the core carbazole (I) represented by the general formula (2) respectively, and $X_1$ in the core carbazole is an alkyl group of carbon number two (ethyl group) and $R_1$ to $R_8$ are hydrogens.

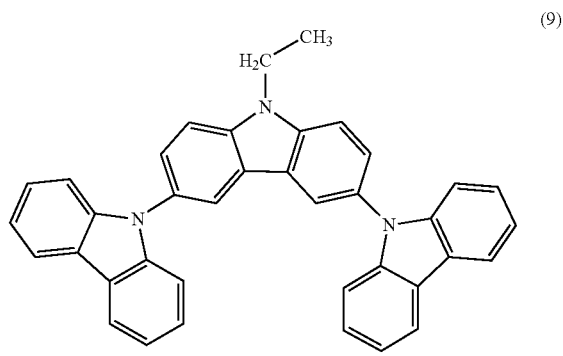

(9)

In the general formula (1), as for the carbazole derivative of a second generation ($G_2$), for example, the structure represented by structural formula (10) can be mentioned. Specifically, it has the structure such that $N_A$ in the internally branched carbazole (Z) represented by the general formula (3) makes covalent bonds with $C_A$ and $C_B$ of the core carbazole (I) represented by the general formula (2) respectively, $N_A$ of the end carbazole (E) represented by the general formula (4) makes covalent bonds with $C_A$ and $C_B$ in the internally branched carbazole respectively, $X_1$ in the core carbazole is an alkyl group with the carbon number of 2 (ethyl group), and $R_1$ to $R_8$ are hydrogens.

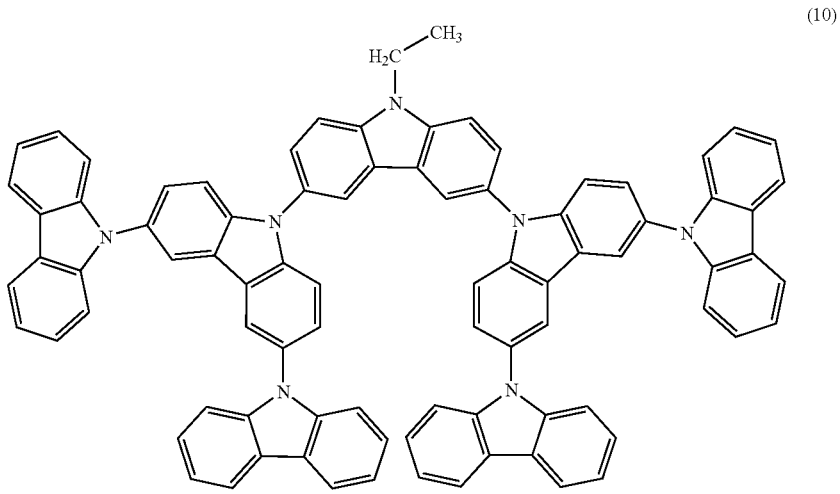

(10)

Further, in the general formula (1), as for the carbazole derivative of a third generation ($G_3$), for example, the structure represented by structural formula (11) can be mentioned. Specifically, it has the structure such that $N_A$ in the internally branched carbazole (Z) represented by the general formula (3) makes covalent bonds with $C_A$ and $C_B$ in the core carbazole (I) represented by the general formula (2) respectively, $N_A$ in another internally branched carbazole (Z') makes covalent bonds with $C_A$ and $C_B$ in the internally branched carbazole respectively, $N_A$ in the end carbazole (E) represented by the general formula (4) makes covalent bonds with $C_A$ and $C_B$ in the internally branched carbazole (Z') respectively, $X_1$ in the core carbazole is an alkyl group with the carbon number of 2 (ethyl group), and $R_1$ to $R_8$ are hydrogens.

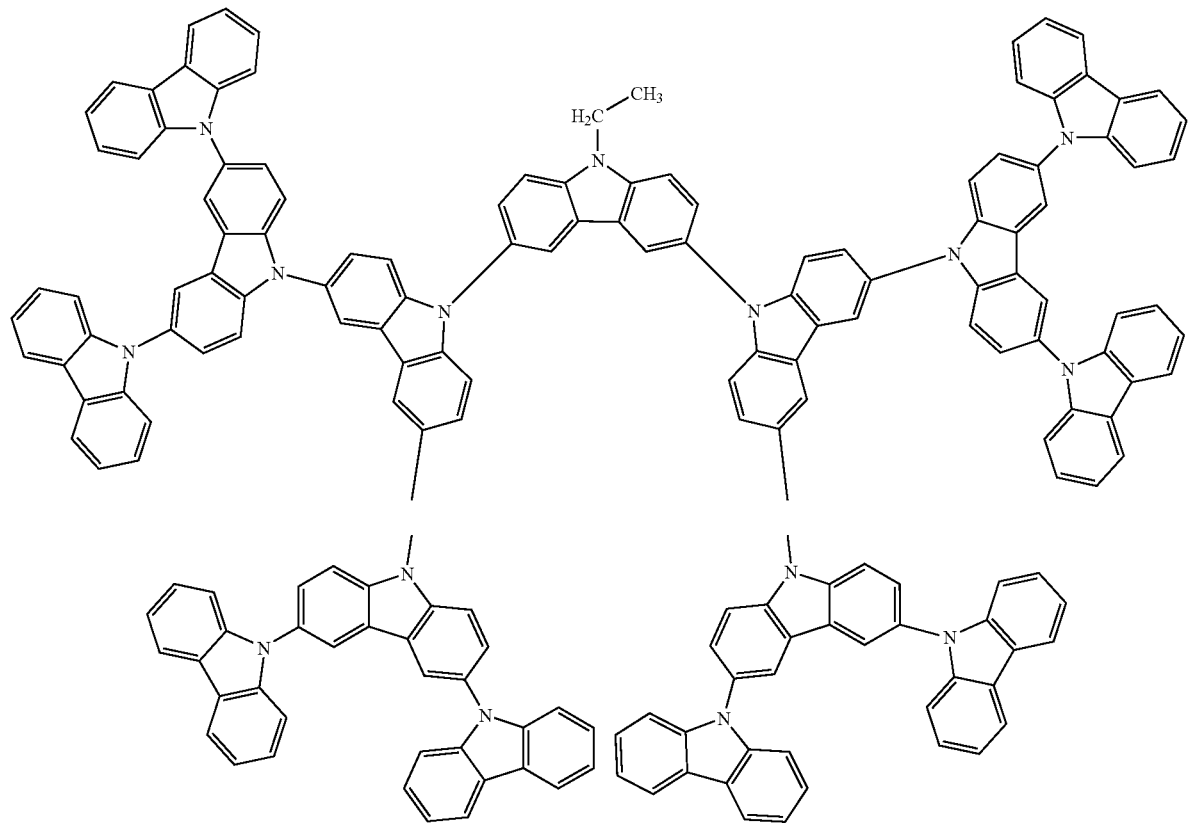

(11)

By increasing generations in such a manner, carbazole derivatives having a dendrimer structure such that the carbazole skeleton continues in a dendritic shape can be formed. Note that, the carbazole derivative of the invention having a dendrimer structure is intended to include dendrimers having a so-called defective structure in a part such that the internally branched carbazole (Z) and end carbazole (E), or the end carbazole (E), are absent in a part after a certain generation among the structure represented by the general formula (1).

Further, as for the carbazole derivative formed in the invention, it is possible to form carbazole derivatives represented by structural formulae (12) to (18) by changing arbitrarily the structure of $R_1$ to $R_8$ in the general formulae (2) to (4).

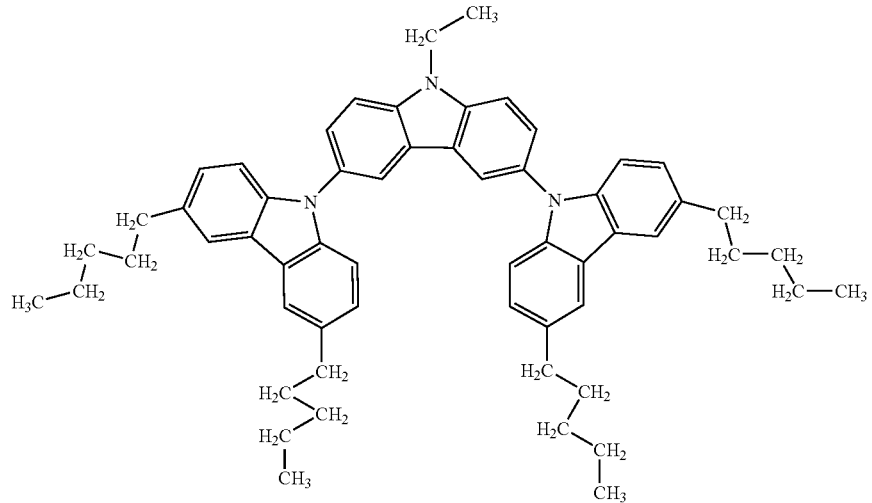
(12)
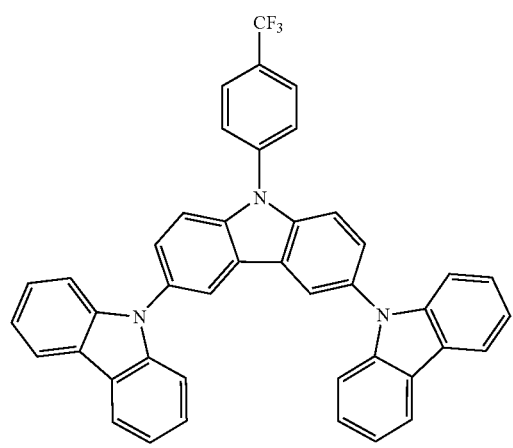
(13)
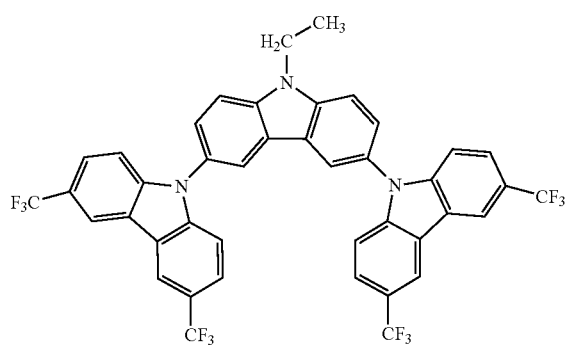
(14)
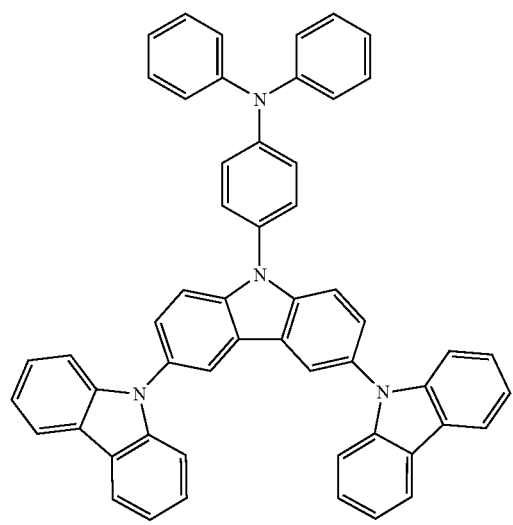
(15)
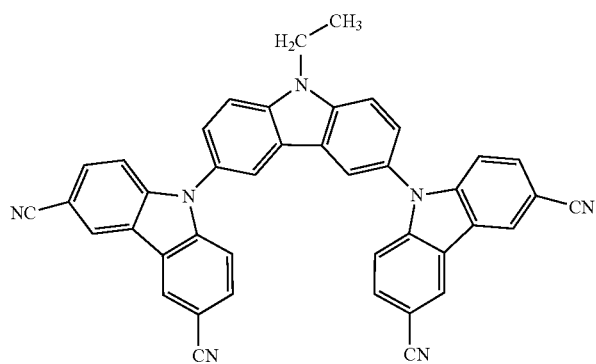
(16)

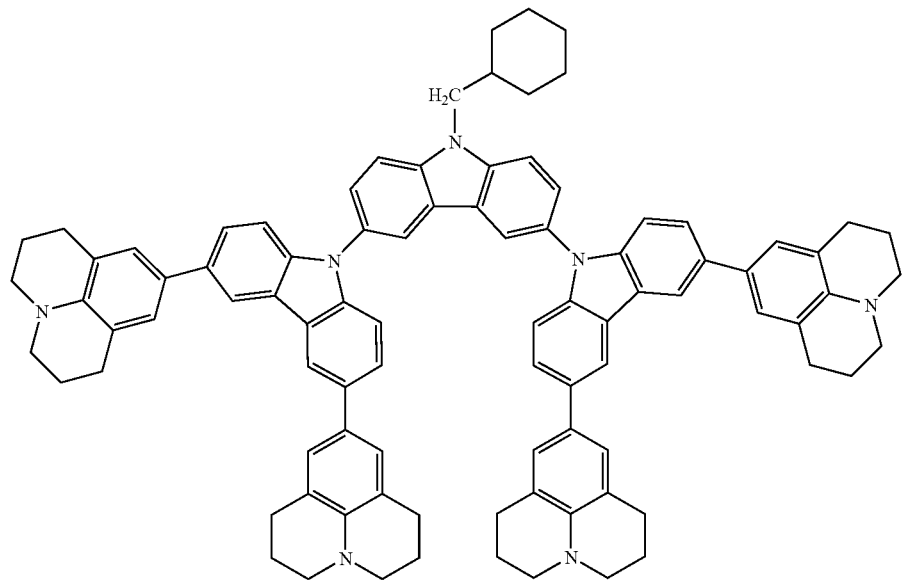

(17)

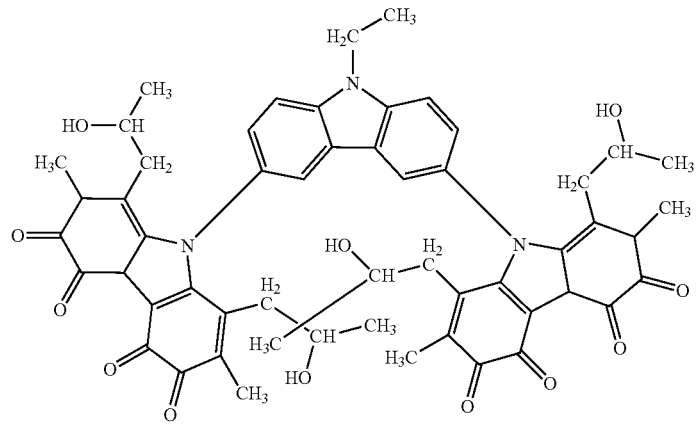

(18)

As for the carbazole derivative including a plurality of first generations ($G_1$) represented by general formulae (5) to (7), for example, the structure represented by chemical formula (19) can be mentioned. Specifically, it has the structure in the case where $N_A$ in the internally branched carbazole (Z) represented by the general formula (3) makes covalent bonds with $C_A$ and $C_B$ in the core carbazole (I) represented by the general formula (2) respectively, $N_A$ in the end carbazole (E) represented by the general formula (4) makes covalent bonds with $C_A$ and $C_B$ in the internally branched carbazole, $X_2$ in the core carbazole is a biphenyl group, $R_1$ to $R_8$ are hydrogens, and k=2.

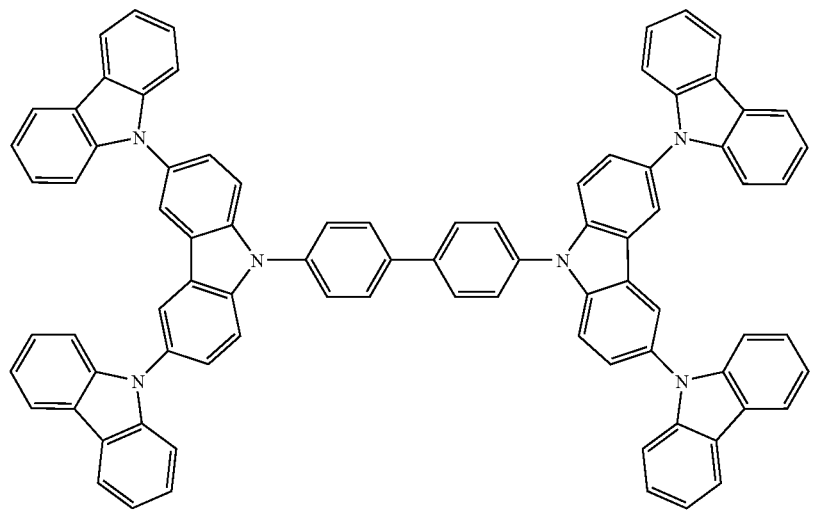

(19)

Furthermore, the carbazole derivative according to the invention can form carbazole derivatives represented by structural formulae (20) to (32) by changing arbitrarily structure of $R_1$ to $R_8$ in the general formulae (2) to (4) and $R_9$ in the aforementioned general formula (6) to any one of heterocyclic residues represented by the structural formula (8).

(20)

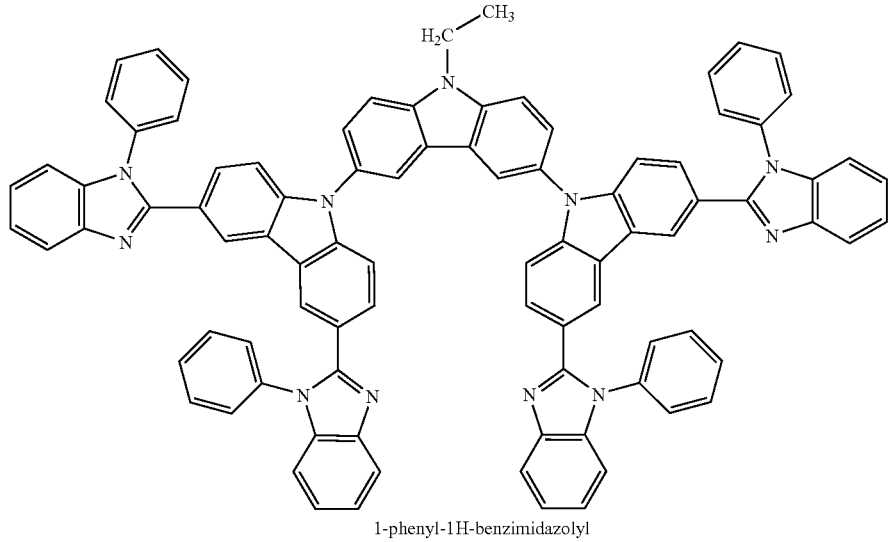

1-phenyl-1H-benzimidazolyl (21)

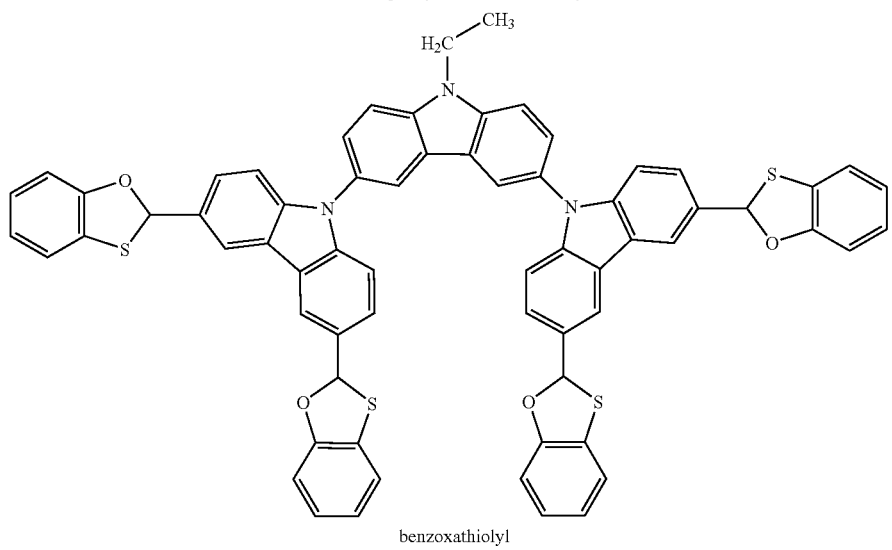

benzoxathiolyl (22)

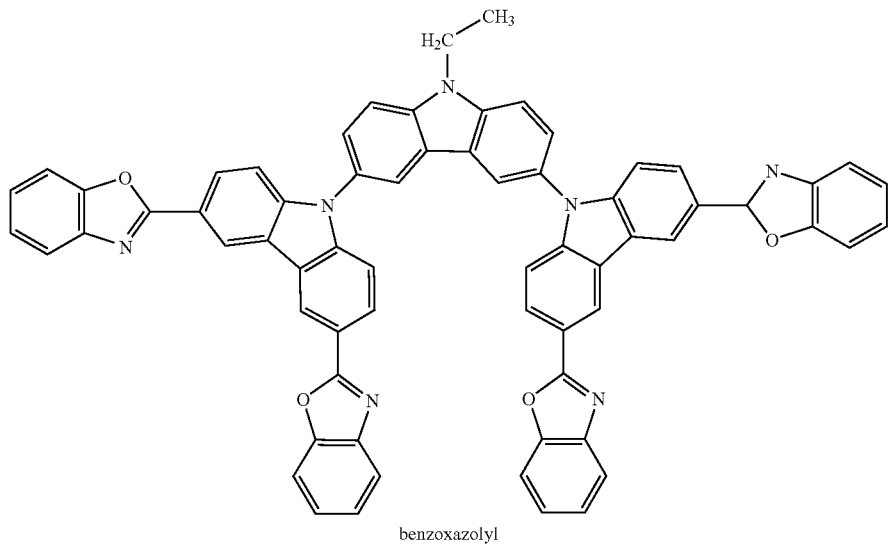

benzoxazolyl

(23)
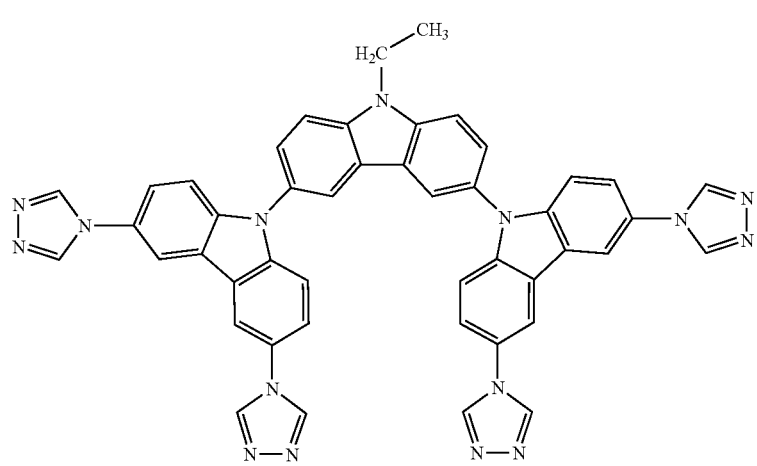
(24)
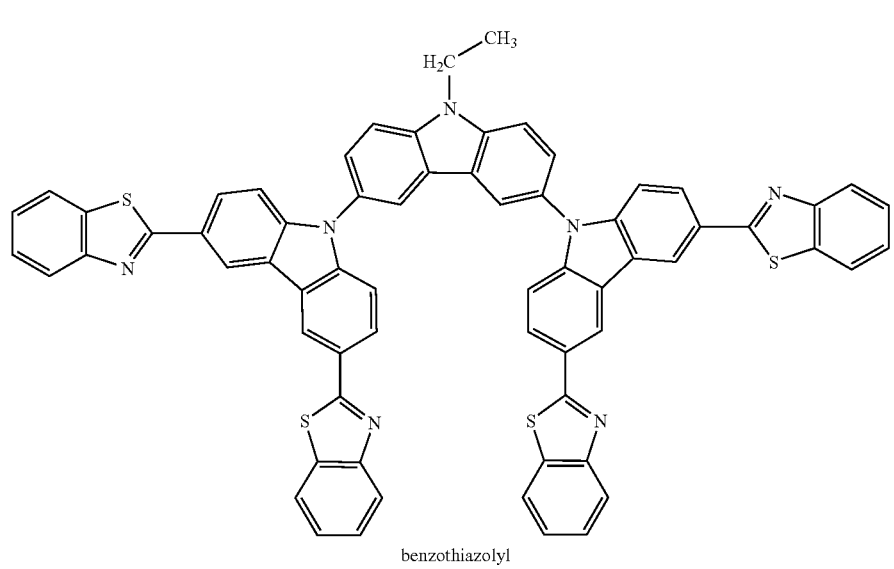
benzothiazolyl
(25)
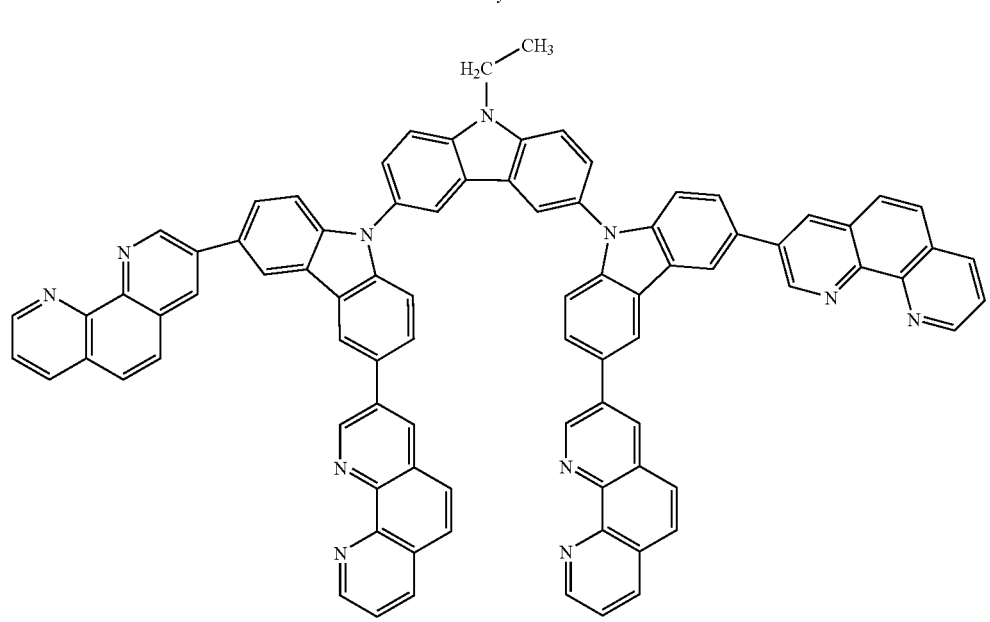

-continued
(26)
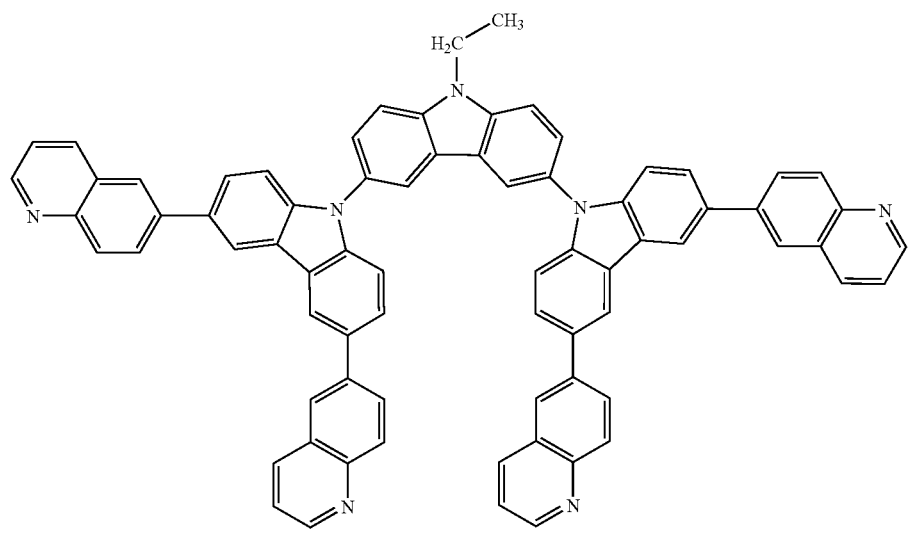
(27)
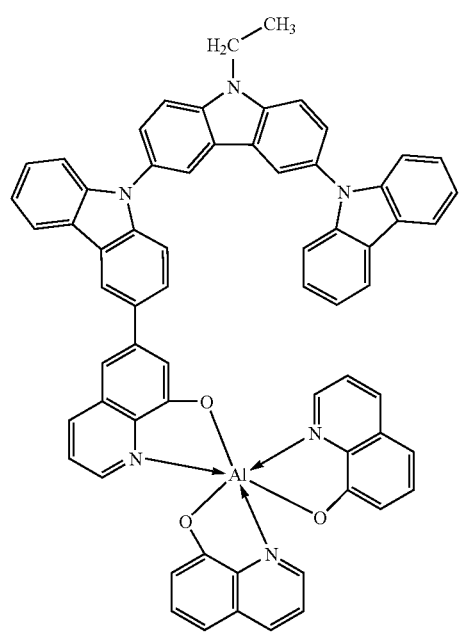
(28)
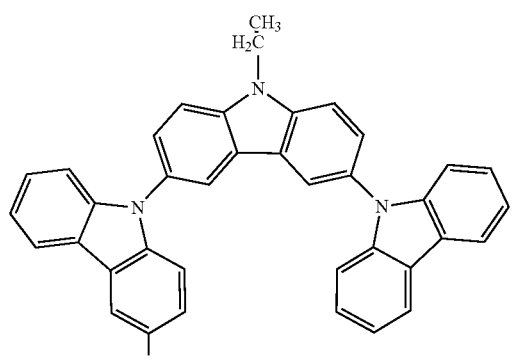

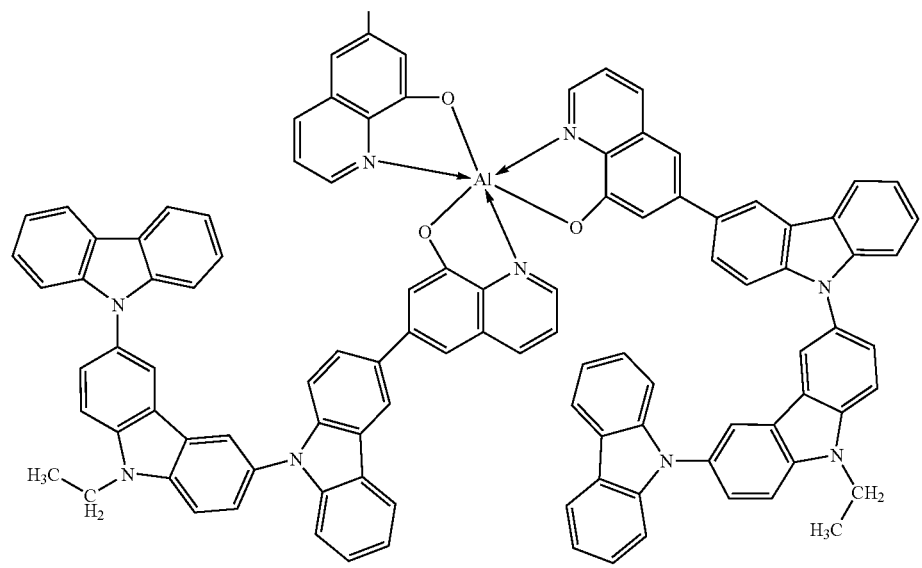
(29)
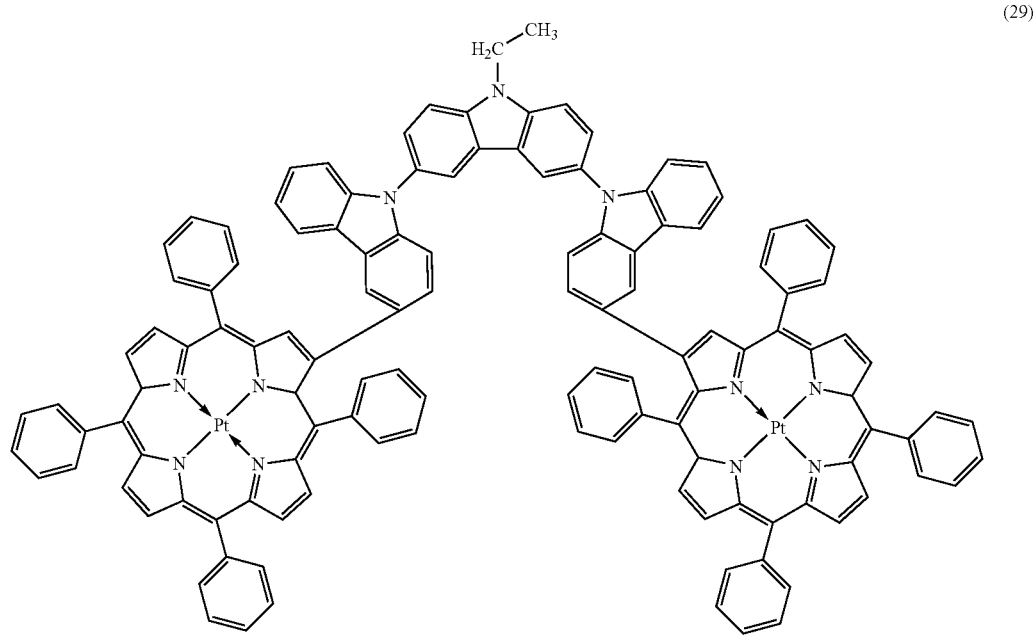

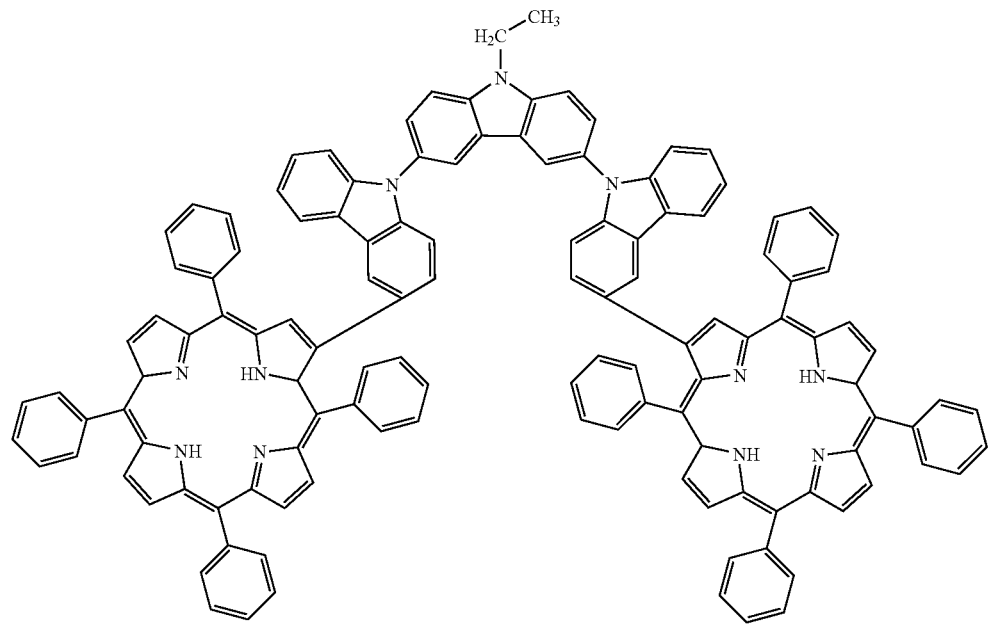
(30)
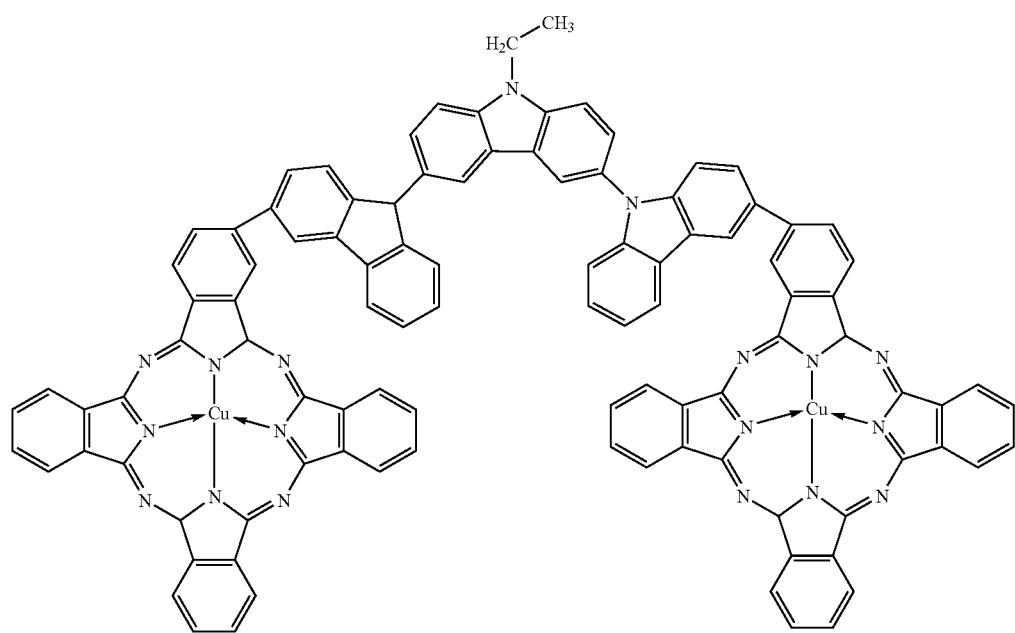
(31)

-continued

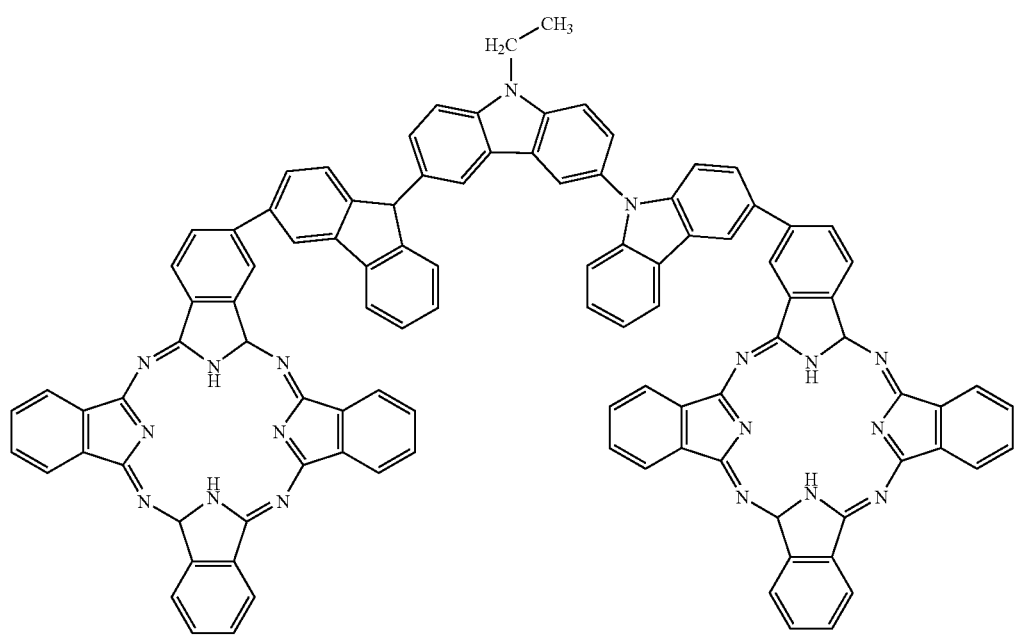

(32)

Note that, the structure represented by the structural formula (8) is a specific example of the heterocyclic residue usable for the invention, which as the usable heterocyclic residue can use an imidazolyl group, an oxathiolyl group, an oxazolyl group, a triazolyl group, a thiazolyl group, a phenanthrolyl group and the like.

The carbazole derivative according to the invention has a dendrimer structure such that the carbazole skeleton continues in a dendritic shape, therefore it has a large molecular weight and forms a steric structure. Accordingly, it has merits of good heat resistivity and difficulty to crystallize (good film forming properties).

Embodiment Mode 2

In the invention, an organic semiconductor element can be formed by employing the carbazole derivative shown in the Embodiment Mode 1. In this connection, use of the carbazole derivative according to the invention having an excellent heat resistivity and being difficult to crystallize upon film formation for a vertical transistor (SIT), in which flatness of a film forming an active layer tends to exert influence on the property of the element among organic semiconductor elements, is effective for accomplishing extension of the lifetime of the organic semiconductor element.

Embodiment Mode 3

Furthermore, in the invention, a light emitting element can be formed by employing the carbazole derivative shown in the Embodiment Mode 1.

The element constitution of the light emitting element in the invention is, basically, a constitution in which a layer containing a light emitting material including the aforementioned carbazole derivative (constituted by combining arbitrarily a hole injecting layer, a hole transporting layer, a light emitting layer, a hole blocking layer, an electron transporting layer, an electron injecting layer and the like) is sandwiched between a pair of electrodes (anode and cathode). The aforementioned carbazole derivative can be employed for the light emitting layer or the hole transporting layer in a light emitting element having a constitution such as anode/hole injecting layer/light emitting layer/electron transporting layer/cathode, anode/hole injecting layer/hole transporting layer/light emitting layer/electron transporting layer/cathode, anode/hole injecting layer/hole transporting layer/light emitting layer/electron transporting layer/electron injecting layer/cathode, anode/hole injecting layer/hole transporting layer/light emitting layer/hole blocking layer/electron transporting layer/cathode, or anode/hole injecting layer/hole transporting layer/light emitting layer/hole blocking layer/electron transporting layer/electron injecting layer/cathode.

The light emitting element according to the invention is preferably supported over a substrate. The substrate is not particularly limited and those used for conventional light emitting elements can be employed, including those made of glass, quartz, transparent plastic or the like. As for anode material for the light emitting element according to the invention, use of metal, alloy or an electroconductive compound having a large work function (work function of 4.0 eV or more), or a mixture thereof is preferred. Specific examples of the anode material include, in addition to ITO (indium tin oxide), IZO (indium zinc oxide) in which indium oxide is mixed with 2 to 20 [%] of zinc oxide (ZnO), gold (Au), platinum (Pt), nickel (Ni), tungsten (W), chromium (Cr), molybdenum (Mo), iron (Fe), cobalt (Co), cupper (Cu), palladium (Pd) or nitride of metal material (TiN).

On the other hand, as for a cathode material, use of metals, alloys or electroconductive compounds having a small work function (work function of 3.8 eV or less), or mixtures thereof are preferred. Specific examples of the cathode material include, in addition to elements in groups I or II of the periodic table of the elements, i.e., alkaline metals such as Li and Cs, alkaline earth metals such as Mg, Ca and Sr, and alloys (Mg:Ag, Al:Li) and compounds (LiF, CsF, $CaF_2$) containing these, transition metals including rare earth metals, and further laminates with metals (including alloys) such as Al, Ag or ITO.

The aforementioned anode material and cathode material are formed into a thin film by an evaporation method, a sputtering method or the like to form the anode and cathode respectively. Film thickness thereof is preferably from 10 to 500 nm.

In the light emitting element according to the invention, the constitution thereof is such that the light generated by the recombination of carriers in the layer containing the light emitting material radiates outside through one of the anode or the cathode, or both of them. That is, when the light is allowed to radiate through the anode, it is formed of a light-transparent material; and when the light is allowed to radiate through the cathode, it is formed of a light-transparent material.

As for a layer containing the light emitting material, publicly known materials may be employed, and either low molecular weight materials or high molecular weight materials may be employed. Note that, the material for forming the layer containing the light emitting material may include not only the material composed of only organic compound materials but also constitutions containing an inorganic compound in a part thereof.

The layer containing the light emitting material is formed by combining and laminating layers such as a hole injecting layer composed of a hole injectable material, a hole transporting layer composed of a hole transportable material, a light emitting layer composed of a light emitting material, a hole blocking layer composed of a hole blocking material, an electron transporting layer composed of an electron transportable material, and an electron injecting layer composed of an electron injectable material.

In the invention, when the carbazole derivative is employed for the light emitting layer, an light emitting element may be also formed by combining a layer containing a light emitting material being formed between a pair of electrodes with a layer other than the light emitting layer to form a laminates. The layer containing the light emitting material in this case may have a constitution in which, in addition to the light emitting layer, a hole injecting layer, a hole transporting layer, a hole blocking layer, an electron transporting layer, an electron injecting layer or the like is combined and laminated according to need. Specific materials employed in this case are shown below.

As for a hole injectable material, as organic compounds, porphyrin-series compounds are effective, and phthalocyanine (hereinafter, shown as $H_2$-Pc), copper phthalocyanine (hereinafter, shown as Cu-Pc) or the like may be employed. There also exist materials formed by performing chemical doping to a conductive high molecular weight compound, and polyethylene dioxythiophene (hereinafter, shown as PEDOT) doped with polystyrene sulfonate (hereinafter, shown as PSS) or the like may be employed.

As for a hole transportable material, aromatic amine-series (that is, those having a benzene ring-nitrogen bond) compounds are preferable. As widely employed materials, for example, in addition to N,N'-bis(3-methylphenyl)-N,N'-diphenyl-[1,1'-biphenyl]-4,4'-diamine (hereinafter, shown as TPD), 4,4'-bis[N-(1-naphthyl)-N-phenyl-amino]-biphenyl (hereinafter, shown as α-NPD) being a derivative thereof, and starburst type aromatic amine compounds such as 4,4',4''-tris(N-carbazolyl)-triphenylamine (hereinafter, shown as TCTA), 4,4',4''-tris(N,N-diphenyl-amino)-triphenylamine (hereinafter, shown as TDATA), or 4,4',4''-tris[N-(3-methylphenyl)-N-phenyl-amino]-triphenylamine (hereinafter, shown as MTDATA) can be mentioned.

As for an electron transportable material, metal complexes having a quinoline skeleton or a benzoquinoline skeleton such as tris(8-quinolinolato)aluminum (hereinafter, shown as $Alq_3$), tris(4-methyl-8-quinolinolato)aluminum (hereinafter, shown as $Almq_3$), or bis(10-hydroxybenzo[h]-quinolinato) beryllium (hereinafter, shown as $BeBq_2$), and a mixed ligand complex such as bis(2-methyl-8-quinolinolato)-(4-hydroxy-biphenylyl)aluminum (hereinafter, shown as BAlq) are preferred. Further, there exist metal complexes having an oxazole-series, a thiazole-series, or a benzimidazole ligand such as bis[2-(2-hydroxyphenyl)-benzoxazolato]zinc (hereinafter, shown as $Zn(BOX)_2$), bis[2-(2-hydroxyphenyl)-benzothiazolato]zinc (hereinafter, shown as $Zn(BTZ)_2$), or tris (2-(2'-hydroxyphenyl)-1-phenyl-1H-benzimidazolate) aluminum (hereinafter, shown as $Al(PBI)_3$).

Furthermore, other than metal complexes, oxadiazole derivatives such as 2-(4-biphenylyl)-5-(4-tert-butylphenyl)-1,3,4-oxadiazole (hereinafter, shown as PBD) or 1,3-bis[5-(p-tert-butylphenyl)-1,3,4-oxadiazole-2-yl]benzene (hereinafter, shown as OXD-7), triazole derivatives such as 3-(4-tert-butylphenyl)-4-phenyl-5-(4-biphenylyl)-1,2,4-triazole (hereinafter, shown as TAZ) or 3-(4-tert-butylphenyl)-4-(4-ethyl-phenyl)-5-(4-biphenylyl)-1,2,4-triazole (hereinafter, shown as p-EtTAZ), phenanthroline derivatives such as vasophenanthroline (hereinafter, shown as BPhen) or vasocuproin (hereinafter, shown as BCP), or benzimidazole derivatives such as 2,2',2''-(1,3,5-benzenetriyl)-tris(1-phenyl-1H-benzimidazole (hereinafter, shown as TPBI), 1,3,5-tris(4,4',4''(1-phenyl-1H-benzimidazolyl)-benzezolyl)-benzene (hereinafter, shown as TPBIBB), or N-phenyl-2,4,5,7-tetrakis(1-phenyl-1H-benzimidazole (hereinafter, shown as PBIC) can be employed.

As for a hole blocking material, the aforementioned BAlq, OXD-7, TAZ, p-EtTAZ, BPhen, BCP or the like can be employed.

Note that, the carbazole derivative may be also employed as a host material or a guest material of the light emitting layer.

As for the guest material when the carbazole derivative is used as the host material of the light emitting layer, in addition to quinacridone, diethylquinacridone (DEQ), rubrene, perylene, DPT, Co-6, PMDFB, BTX, ABTX, DCM or DCJT, a triplet light emitting material (phosphorescent material) such as tris(2-phenylpyridine) iridium (hereinafter, shown as $Ir(ppy)_3$) or 2,3,7,8,12,13,17,18-octaethyl-21H,23H-porphyrin platinum (hereinafter, shown as PtOEP) can be employed.

On the other hand, as for the host material when the carbazole derivative is used as the guest material of the light emitting layer, TPD, α-NPD, TCTA, PBD, OXD-7, BCP or the like can be employed.

Furthermore, in the invention, when the carbazole derivative is employed for a hole transporting layer, the layer containing the light emitting material is obtained by laminating a hole transporting layer containing the carbazole derivative being formed at least on the anode side, a light emitting layer and an electron transporting layer formed on the cathode side to form. In this case, as for the light emitting material employed for the light emitting layer, specifically, in addition to metal complexes such as $Alq_3$, $Almq_3$, $BeBq_2$, BAlq, $Zn(BOX)_2$ and $Zn(BTZ)_2$, various fluorescent dyes are effective.

As described above, by forming a light emitting element employing the carbazole derivative according to the invention having material properties such as excellent in heat resistance and hole transportability and difficult to crystallize when formed into a film, it is possible to accomplish to decrease the drive voltage and extend the lifetime of the light emitting element.

Embodiment 1

Synthesis Examples of the carbazole derivative according to the invention and Embodiments will be described bellow. However, the invention is not limited to these examples.

SYNTHESIS EXAMPLE 1

Synthetic Method of N-ethyl-3,6-di(N-carbazolyl)carbazole

Figure 13:
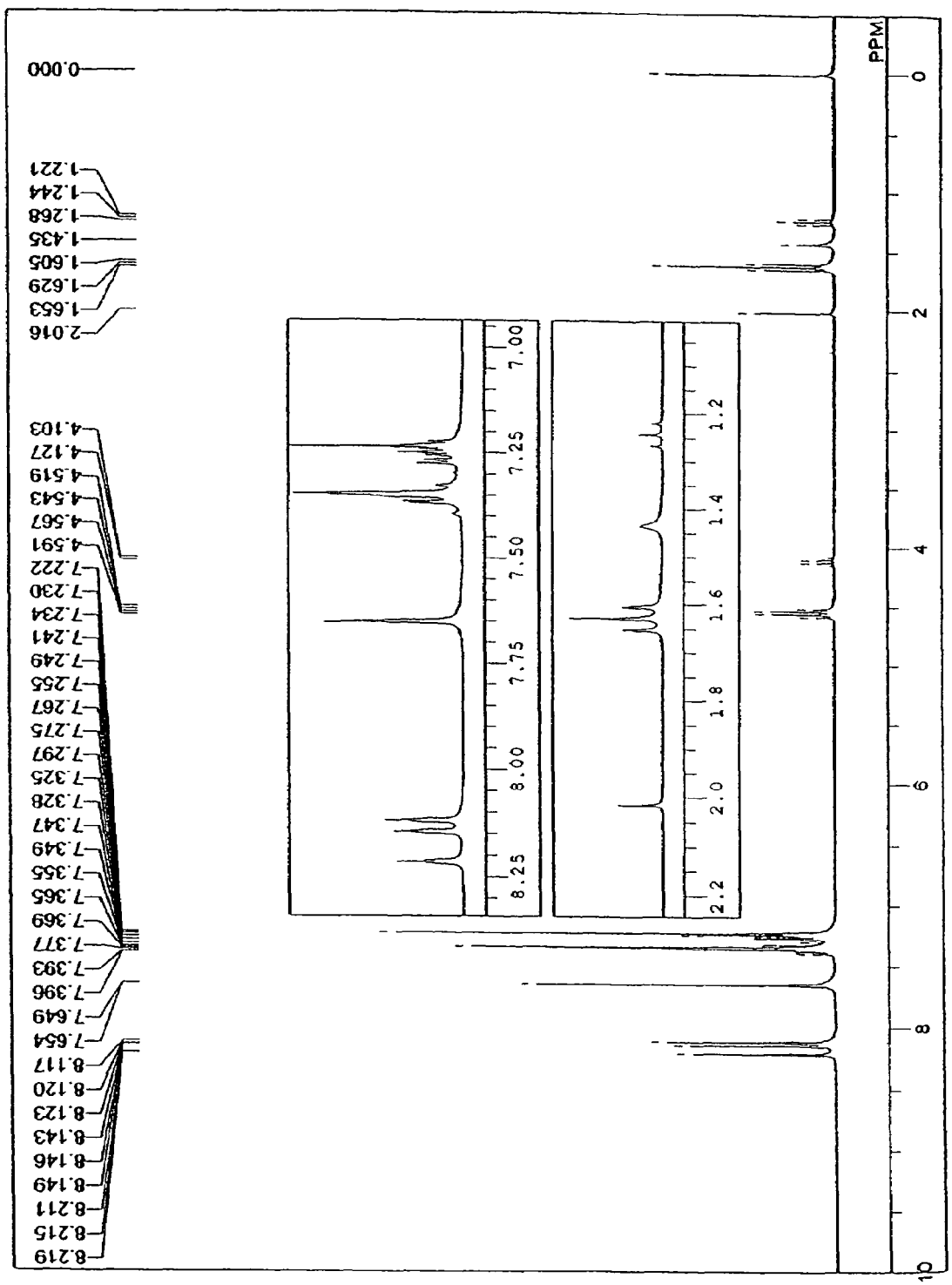
FIG. 13 shows $^1$H NMR data of the carbazole derivative according to the invention.
Figure 14:
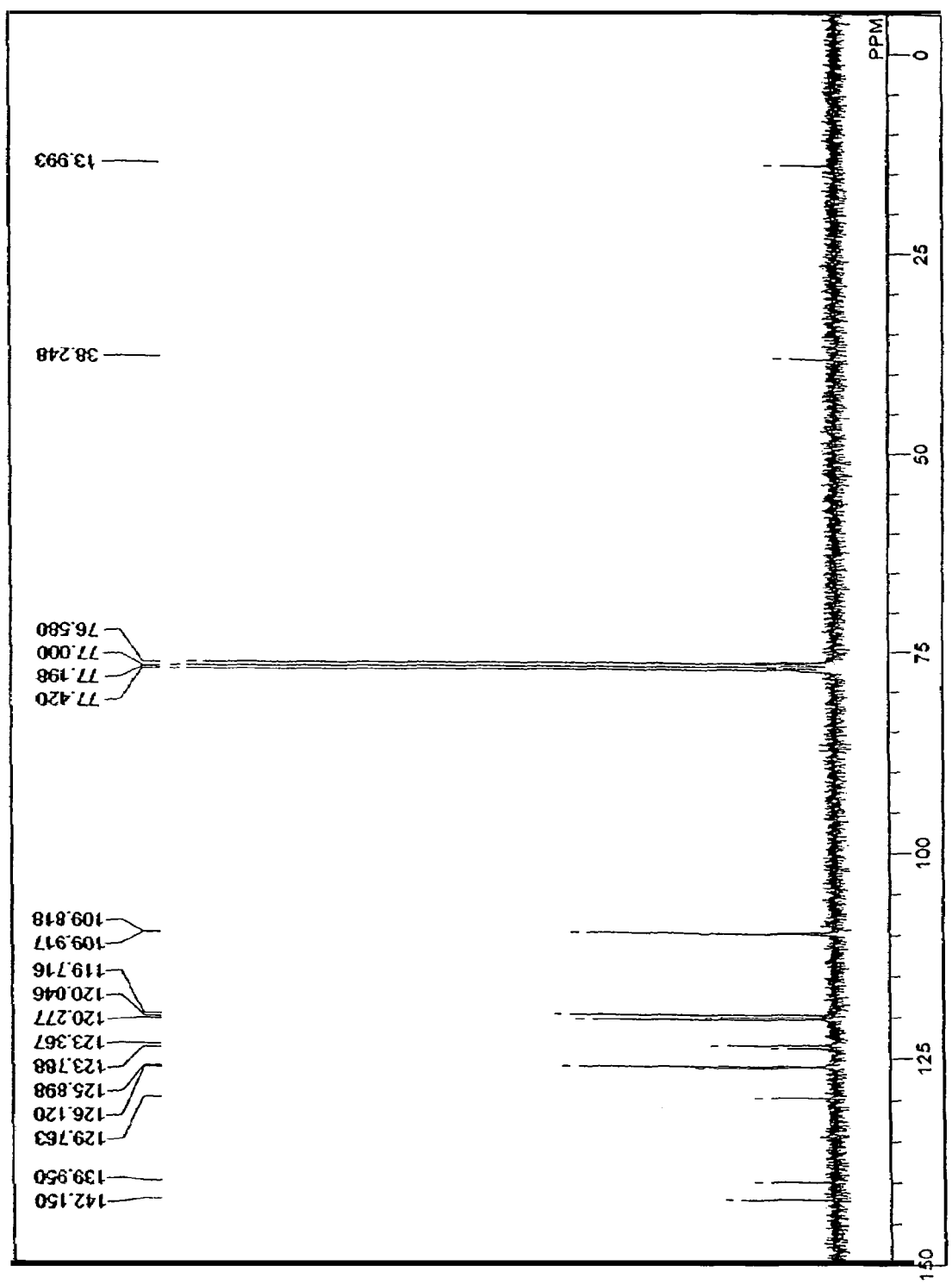
FIG. 14 shows $^{13}$C NMR data of the carbazole derivative according to the invention.

A suspension of N-ethyl-3,6-bromocarbazole (3.53 g, 10 mmol), carbazole (3.51 g, 21 mmol) and sodium t-butoxide (2.88 g, 30 mmol) in toluene was subjected to freeze deaeration. In an atmosphere of an inert gas such as argon or nitrogen, 0.22 g (0.4 mmol) of bis(dibenzylidene acetone)palladium (0) (Pd(dba)$_2$) and 1.2 g (0.6 mmol) of a 10% tri-t-butylphosphine hexane solution were added and stirred for 6 hours at 80° C. After adding water, diethyl ether was added to be stirred. The precipitate was filtrated in a reduced pressure, and the residuum of the filtration was dried in a reduced pressure. The obtained solid was recrystallized by using a mixed solvent of ethyl acetate and chloroform to give the compound in the title being cream-colored powder at a yield of 57% (chemical formula (9)). It had a melting point at 300° C., showed a sublimation point at 385° C. under normal pressure, had a glass transition point (Tg) at 138° C., and crystallization temperature at 182° C. Further, it had a HOMO level of −5.57 eV and LUMO level of −2.31 eV. The compound can be formed into a uniform film over a substrate by using a vacuum evaporation method. NMR data thereof are shown in FIG. 13 ($^1$H NMR) and FIG. 14 ($^{13}$C NMR).

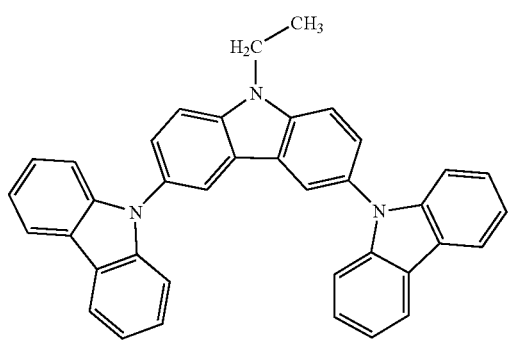

(9)

$^1$H NMR(300 MHz, CDCl$_3$) δ 1.62(t, J=7.2 Hz, 3H), 4.55 (q, J=7.2 Hz, 2H), 7.22-7.40(m, 12H), 7.65(d, J=1.2 Hz, 4H), 8.13(d, J=7,5 Hz, 4H), 8.22(s, 2H). $^{13}$C NMR(75.5 MHz, CDCl$_3$) δ 14.1, 38.2, 109.7, 109.9, 119.6, 119.9, 120.3, 123.1, 123.5, 125.8, 126.0, 129.4, 139.7, 141.9.

Figure 8:
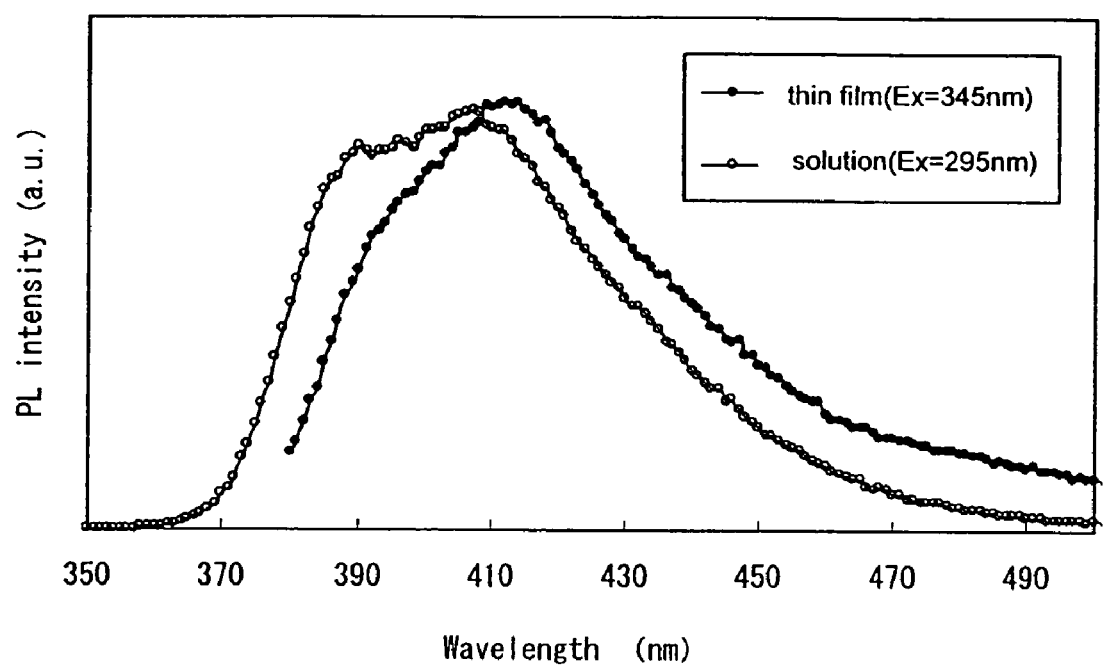
FIG. 8 shows fluorescent spectra of the carbazole derivative according to the invention.

Measurement of a fluorescent spectrum for a thin film and a solution (sovlent: dichloromethane) of N-ethyl-3,6-di(N-carbazolyl)carbazole gave the fluorescent spectrum having the largest peak at 413 nm for an exciting wavelength (345 nm) in the case of the thin film, and the fluorescent spectrum having the largest peak at 407 nm for an exciting wavelength (295 mn) in the case of the solution (FIG. 8).

Figure 9:
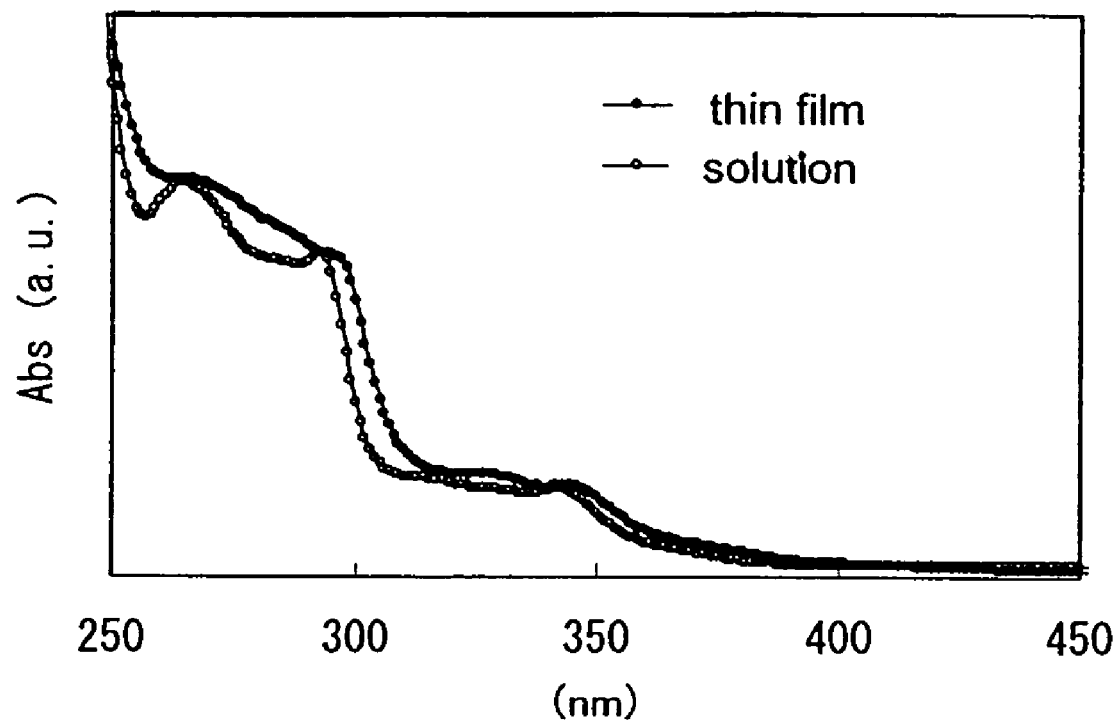
FIG. 9 shows UV-visible region absorption spectra of the carbazole derivative according to the invention.

Measurement of a UV-visible region absorption spectrum for the thin film and the solution (solvent: dichloromethane) of N-ethyl-3,6-di(N-carbazolyl)carbazole gave the largest absorption wavelength at 344 nm in the case of the thin film, and the largest absorption wavelength at 342 nm in the case of the solution (FIG. 9).

In this Embodiment, an element construction will be explained about the case where a light emitting element is produced by employing the carbazole derivative according to the invention for a part of a layer containing a light emitting material, specifically, about the case where the carbazole derivative according to the invention is employed as the host material of a light emitting layer in a layer containing a light emitting material by using FIG. 1.

First, a first electrode 101 of a light emitting element is formed over a substrate 100. In the Embodiment, the first electrode 101 functions as an anode. It is formed by employing ITO, which is a transparent conductive film, as the material and by a sputtering method in a film thickness of 110 nm.

Next, a layer 102 containing a light emitting material is formed over the first electrode (anode) 101. The layer 102 in the Embodiment containing the light emitting material has a laminated structure composed of a hole injecting layer 111, a hole transporting layer 112, a light emitting layer 113, a hole blocking layer 114 and an electron transporting layer 115.

The substrate on which the first electrode 101 has been formed is fixed to a substrate holder of a commercially available vacuum evaporation apparatus with the face formed of the first electrode 101 downward, copper phthalocyanine (hereinafter, shown as Cu-Pc) is put in an evaporation source provided in the vacuum evaporation apparatus, and the hole injecting layer 111 is formed by an evaporation method utilizing a resistance heating method in a film thickness of 20 nm. As for the material for forming the hole injecting layer 111, publicly known hole injectable materials can be employed.

Next, the hole transporting layer 112 is formed with a material excellent in a hole transportability. As for the material for forming the hole transporting layer 112, publicly known hole transportable materials can be employed and, in this Embodiment, 4,4'-bis[N-(1-naphthyl)-N-phenylamino] biphenyl (hereinafter, shown as α-NPD) is formed into the layer having a thickness of 30 nm by the similar method.

Next, the light emitting layer 113 is formed. In the light emitting layer 113, a hole and an electron recombine to generate light emission. In this Embodiment, among materials forming the light emitting layer 113, the carbazole derivative according to the invention is employed for the host material, which is coevaporated with a publicly known guest material to form the layer. In the Embodiment, N-ethyl-3,6-di(N-carbazolyl)carbazole (hereinafter, shown as EtCz$_2$Cz) shown by the chemical formula (9) is employed as a carbazole derivative employed for the host material, tris(2-phenylpyridine) iridium (hereinafter, shown as Ir(ppy)$_3$), which is an iridium complex, is employed as a guest material, and they are formed into the layer having a thickness of 20 nm by co-evaporation method so that the Ir(ppy)3 becomes 3 wt %.

Next, the hole blocking layer 114 is formed. As for the material to form the hole blocking layer 114, a publicly known electron transportable material can be employed and, in the Embodiment, BCP is employed to form the layer having a thickness of 10 nm by an evaporation method.

Next, the electron transporting layer 115 is formed. As for the material to form the electron transporting layer 115, a publicly known electron transportable material can be employed and, in the Embodiment, Alq$_3$ is employed to form the layer having a thickness of 40 nm by an evaporation method.

Thus, after forming the layer 102 containing the light emitting material formed by laminating the hole injecting layer 111, the hole transporting layer 112, the light emitting layer 113, the hole blocking layer 114 and the electron transporting layer 115, a second electrode 103, which functions as a cathode, is formed by a sputtering method or an evaporation method. In this Embodiment, the second electrode 103 is obtained by forming an alminum:lithium alloy (Al:Li) (100 nm) over the layer 102 containing the light emitting material by an evaporation method.

As mentioned above, the light emitting element employing the carbazole derivative according to the invention is formed.

Note that, the carbazole derivative according to the invention allows the HOMO level of the layer formed by employing the same to be lowered and the whole energy gap to be widened. Accordingly, as shown in the Embodiment, the employment of the carbazole derivative according to the invention as a host material being required of the wideness of the energy gap is highly effective. In addition, since the carbazole derivative has an excellent heat resistance and is difficult to crystallize when formed into a film, extension of the lifetime of the light emitting element can be accomplished.

Embodiment 2

In the Embodiment, a carbazole derivative according to the invention differing from that in Embodiment 1, and an example of a guest material for the light emitting layer employing the same will be shown.

SYNTHETIC EXAMPLE 2

Synthesis of N-phenyl-3,6-di(N-carbazolyl)carbazole 24.3 g (100 mmol) N-phenyl-3,6-dibromocarbazole in a glacial acetic acid (500 mL) solution was added with 44.9 g (200 mmol) of N-iodine succinimide to be stirred overnight at room temperature. An aqueous sodium hydrogencarbonate solution was added to the reaction mixture until the liquid properties became neutral. The mixture was filtrated and the obtained solid was washed with water and dried to give N-phenyl-3,6-diiodinecarbazole (hereinafter, shown as PhI2Cz) with a yield of 85%.

Figure 15:
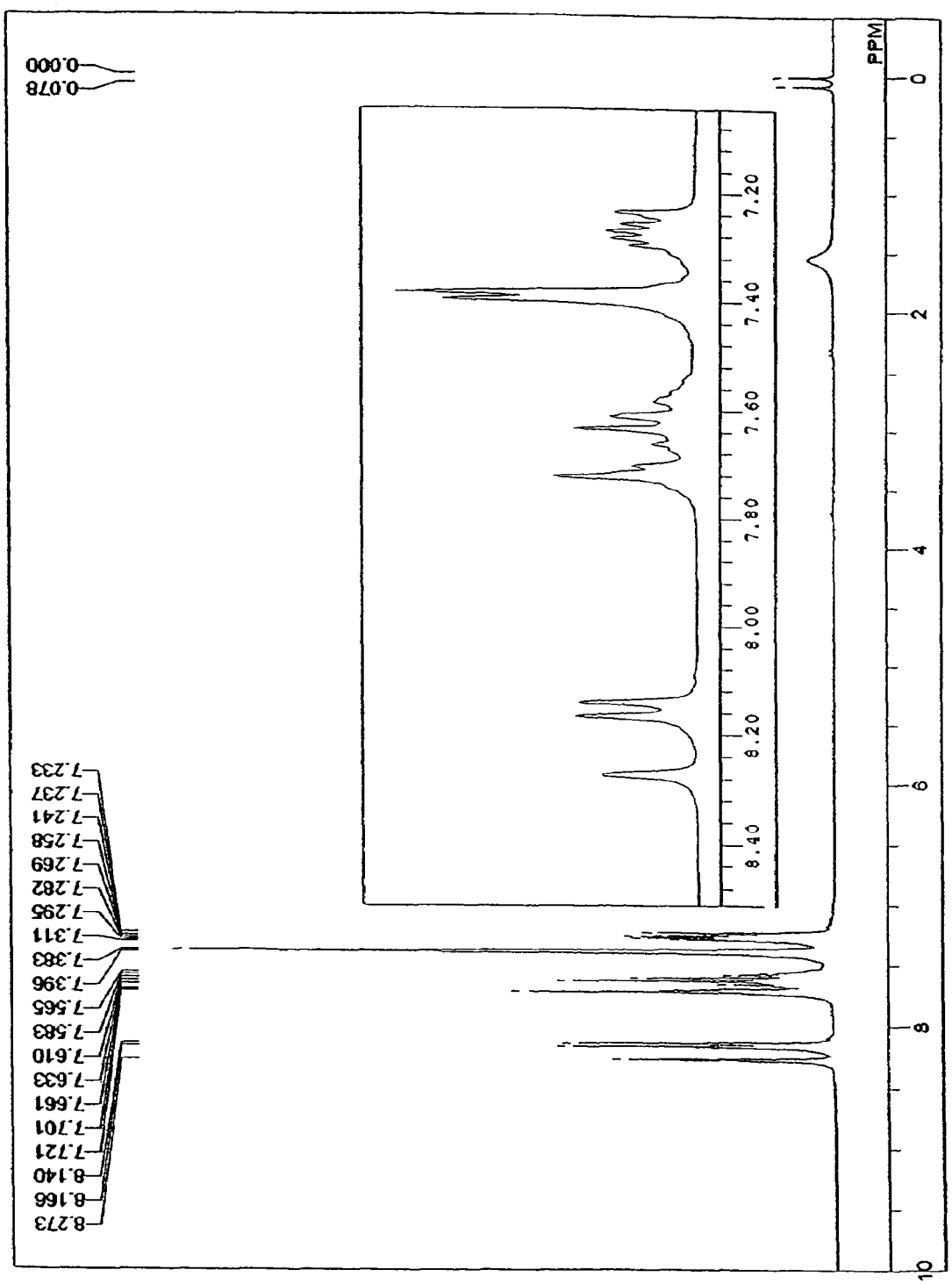
FIG. 15 shows $^1$H NMR data of the carbazole derivative according to the invention.
Figure 16:
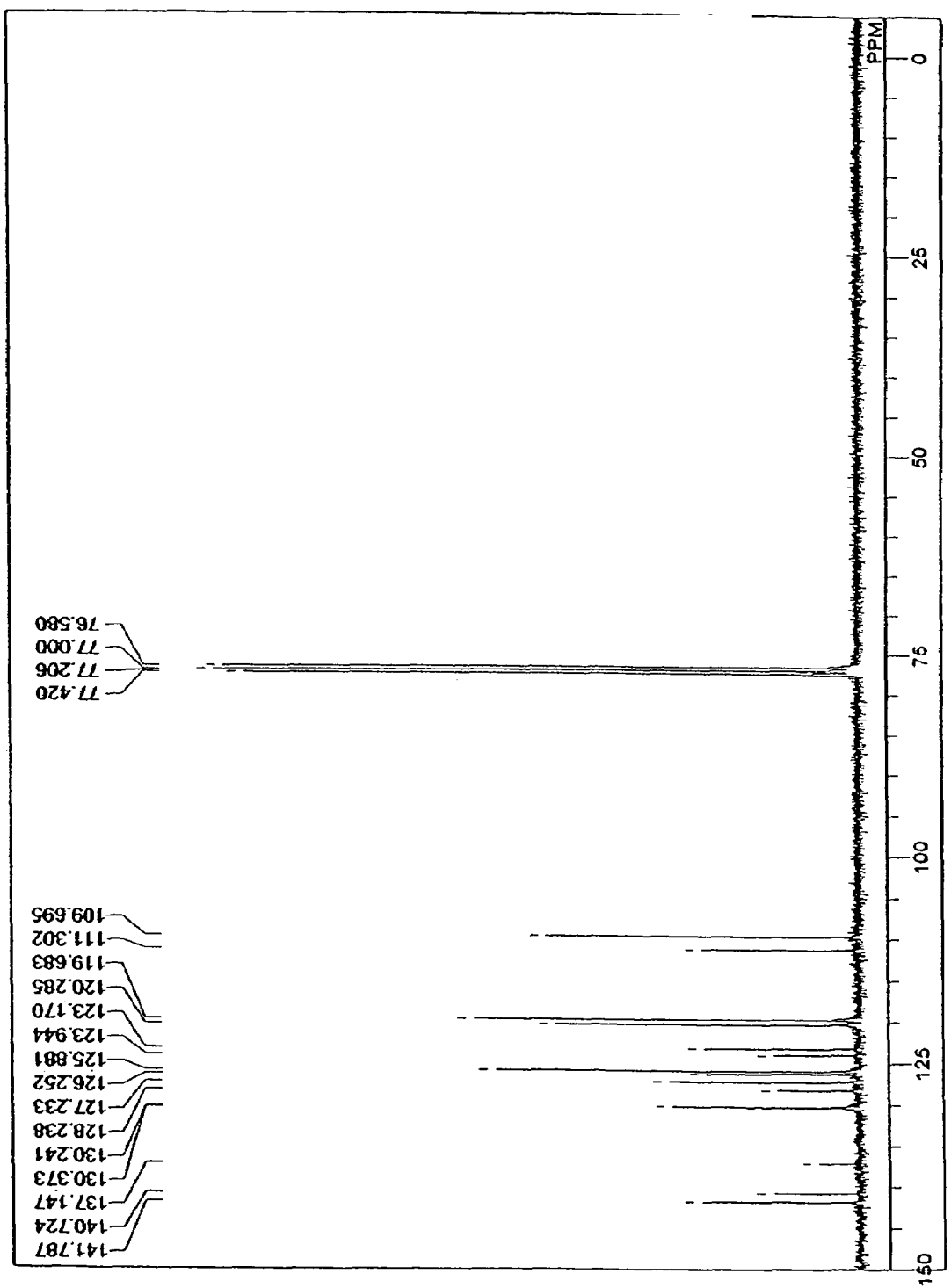
FIG. 16 shows $^{13}$C NMR data of the carbazole derivative according to the invention.

By using the obtained PhI2Cz, a coupling reaction was performed with carbazole in the similar manner as described in the synthesis of N-ethyl-3,6-di(N-carbazolyl)carbazole to give the compound in the title, N-phenyl-3,6-di(N-carbazolyl)carbazole as a beige solid (yield: 85%). NMR data are shown in FIG. 15 ($^1$H NMR) and FIG. 16 ($^{13}$C NMR).

$^1$H NMR(300 MHz, CDCl$_3$) δ 7.20-7.80(m, 21H), 8.15(d, J=7.8 Hz, 4H), 8.27(s, 2H).

$^{13}$C NMR(75.5 MHz, CDCl$_3$) δ 109.7, 111.3, 119.7, 120.3, 123.2, 123.9, 125.9, 126.3, 127.2, 128.2, 130.2, 130.4, 137.1, 140.7, 141.8.

Figure 10:
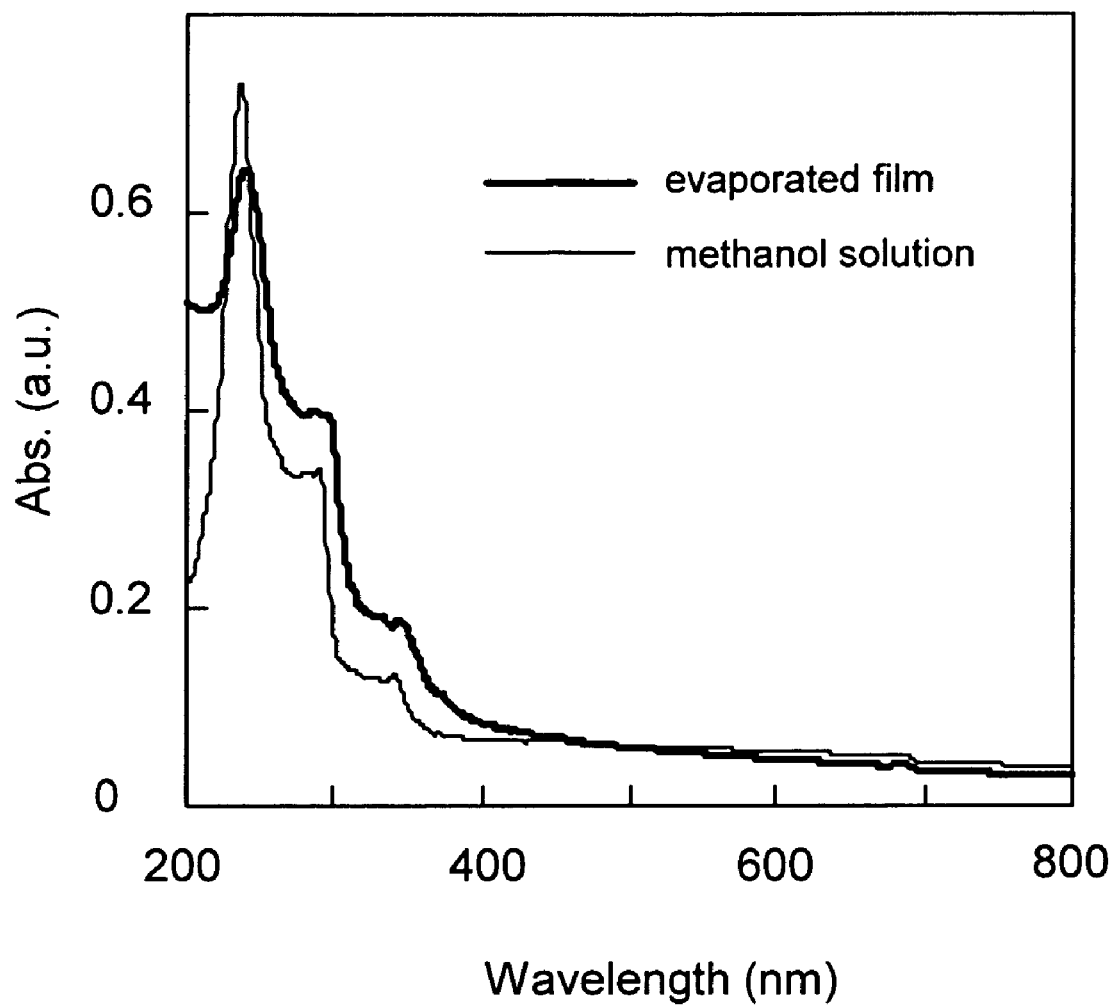
FIG. 10 shows absorption spectra of the carbazole derivative according to the invention in a methanol solution and in an evaporated film.
Figure 11:
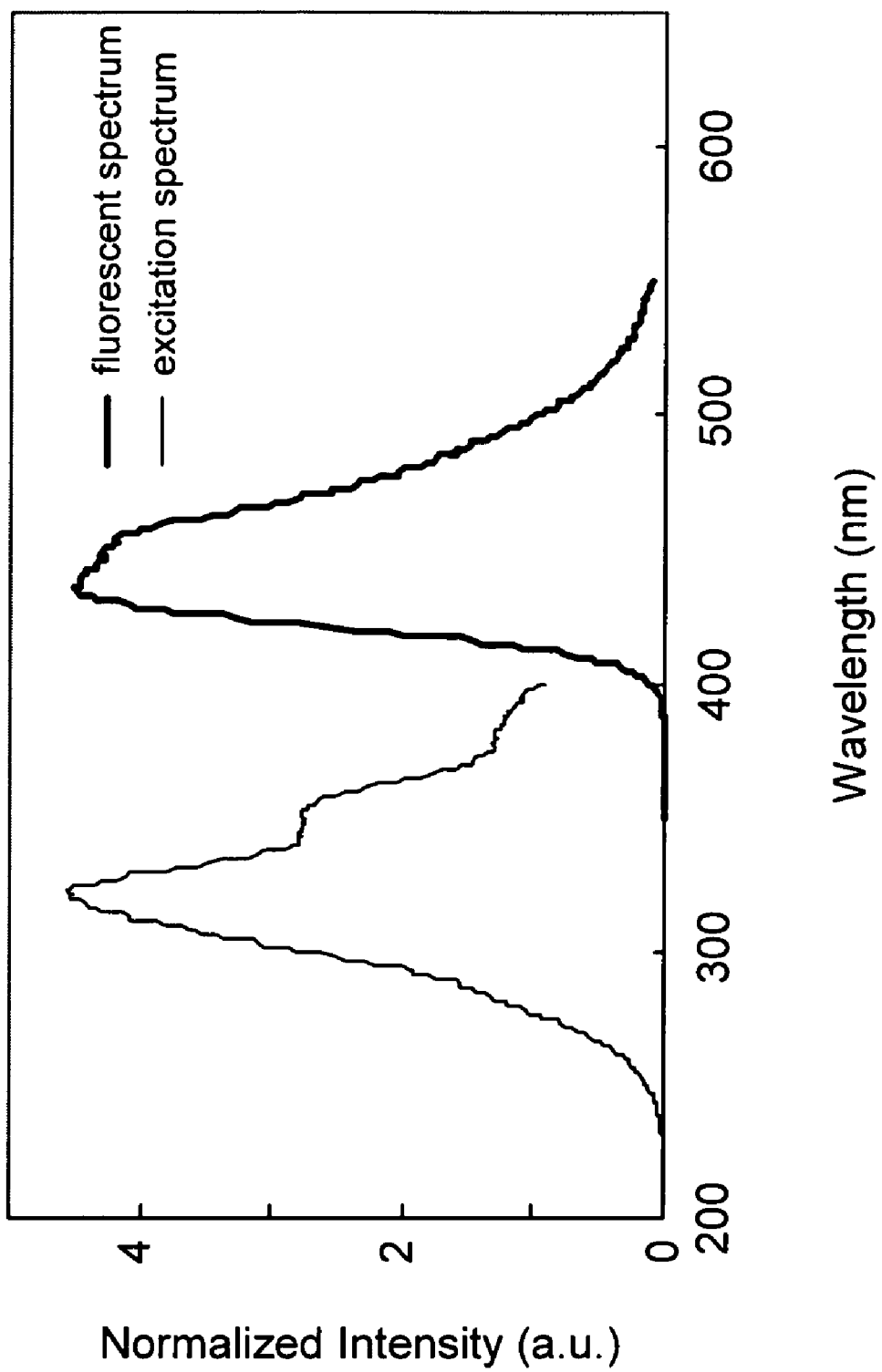
FIG. 11 shows a fluorescent spectrum and an excitation spectrum of the carbazole derivative according to the invention in a methanol solution.

It had the melting point at 283° C. and showed the sublimation point at 410° C. under normal pressure. Formation of a uniform film over a substrate by a vacuum evaporation method was confirmed. Absorption maximum was at 341 nm in methanol and 344 nm for the evaporated film. It was fluorescent, showing the maximum of fluorescence at 435 nm in methanol and 409 nm for the evaporated film. The HOMO level was at −5.64 eV, and the LUMO level was at −2.33 eV. The absorption spectra for the methanol solution and evaporated film are shown in FIG. 10. The respective fluorescent spectrum and excitation spectrum are shown in FIG. 11.

SYNTHETIC EXAMPLE 3

Synthesis of 3,6-di(N-carbazolyl)carbazole

Under a nitrogen atmosphere, 3,6-dibromocarbazole (9.75 g, 30 mmol) was slowly added to a suspension of sodium hydride (45 mmol) in dried THF (100 mL), and then stirred for 30 minutes at room temperature. Benzylbromide (6.72 g, 40 mmol) was dropped into the reaction mixture to be stirred for 20 hours. After addition of water (about 100 mL), a precipitated solid was filtrated, and the filtrate (residuum of the filtration) was washed with an aqueous sodium hydrogencarbonate solution, and then was dissolved in ethanol. The solution was dried by magnesium sulfate, filtrated and concentrated. The residuum was recrystallized with ethanol to give N-benzyl-3,6-dibromocarbazole as a white solid. The yield was 61%.

The obtained N-benzyl-3,6-dibromocarbazole was allowed to couple with carbazole in the same manner as described in synthesis of N-ethyl-3,6-dibromocarbazole (Embodiment 1) to give N-benzyl-3,6-di(N-carbazolyl)carbazole. The yield was 70%.

Figure 17:
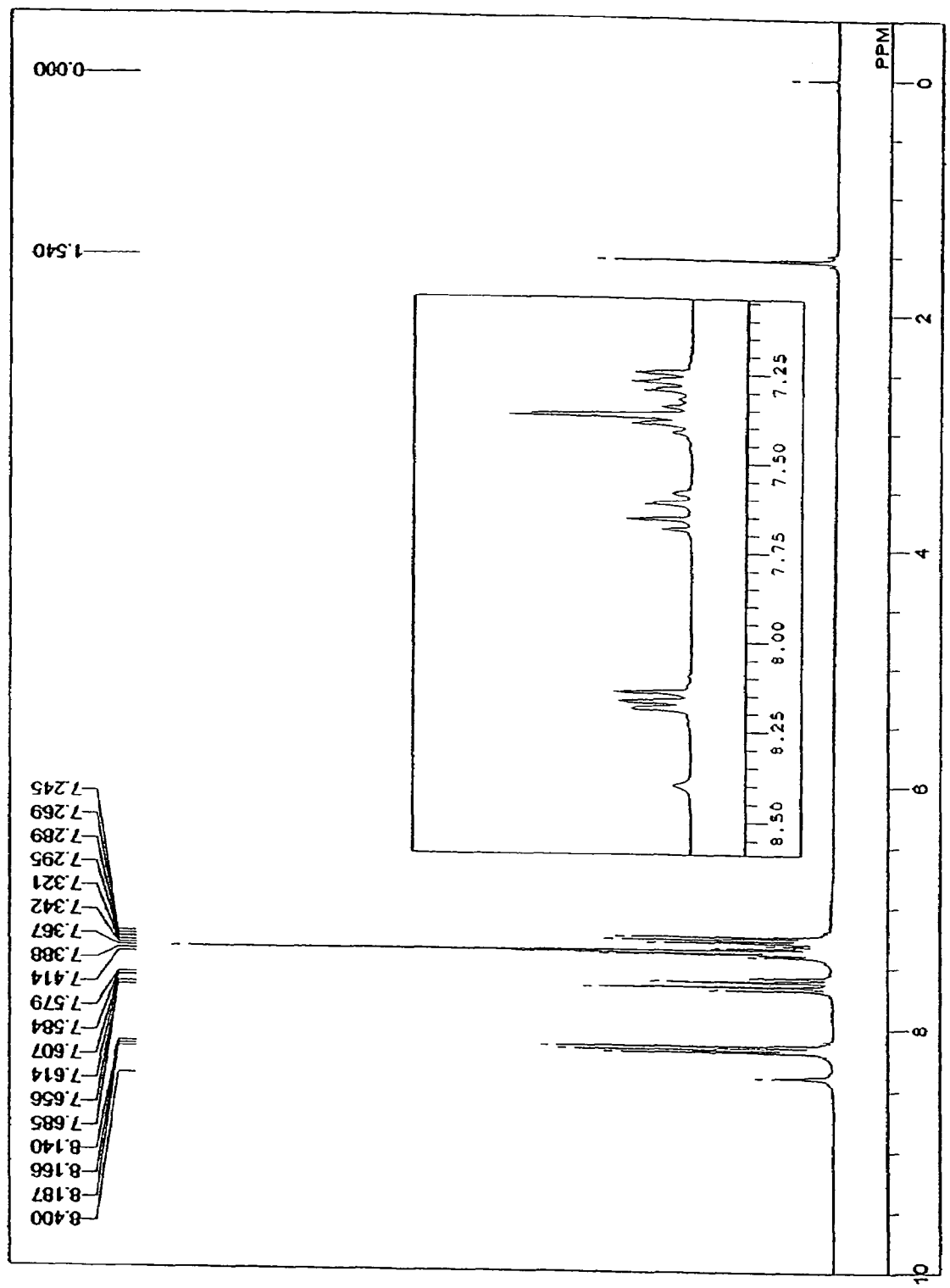
FIG. 17 shows $^1$H NMR data of the carbazole derivative according to the invention.
Figure 18:
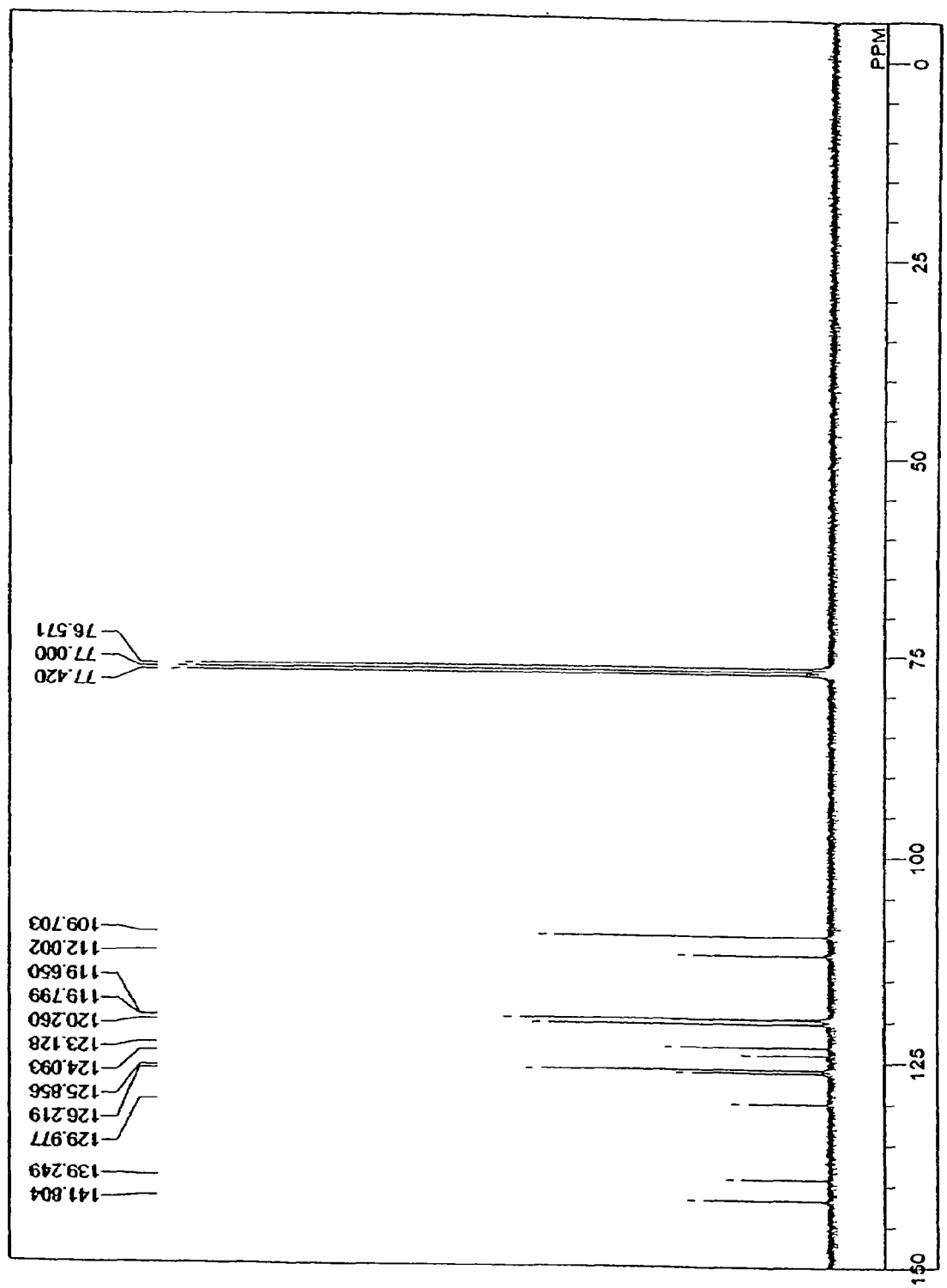
FIG. 18 shows $^{13}$C NMR data of the carbazole derivative according to the invention.

Under a nitrogen atmosphere, a suspension of N-benzyl-3,6-di(N-carbazolyl)carbazole (2.06 g, 3.5 mmol), benzylideneaniline (1.27 g, 7.0 mmol) and t-BuOK (5.06 g, 50 mmol) in a dried DMF (30 mL) was stirred at 75° C. for 4 hours. Water (about 150 mL) was added and black tar precipitated was filtrated. The tar-like material was dissolved in hot chloroform, to which anhydrous magnesium sulfate and activated carbon were added to be stirred for 30 minutes with heating. The mixture was filtrated, the filtrated liquid was concentrated, and then the residuum was recrystallized with chloroform/ethanol to give the compound in the title, (3,6-di(N-carbazolyl)carbazole) as beige powder. The yield was 29%. The melting point was 185 to 187° C. NMR data are shown in FIG. 17 ($^1$H NMR) and FIG. 18 ($^{13}$C NMR).

$^1$H NMR(300 MHz, CDCl$_3$) δ 7.25-7.42(m, 12H), 7.58-7.61(m, 2H), 7.67(d, J=8.7 Hz, 2H), 8.15(d, J=7.8 Hz, 4H), 8.18(d, J=1.5 Hz, 2H), 8.40(s, 1H). $^{13}$C NMR(75.5 MHz, CDCl$_3$) δ 109.7, 112.0, 119.7, 120.0, 120.3, 123.1, 124.0, 125.9, 126.2, 130.0, 139.3, 141.8.

EXAMPLE OF ELEMENT FORMATION

Formation of an Element Employing N-phenyl-3,6-di(N-carbazolyl)carbazole as a Hole Transportable Material A film of copper phthalocyanine, which is a hole injecting material, was formed over a glass substrate on which an ITO film had been formed with vacuum evaporation. The film thickness was 200 nm.

Figure 12:
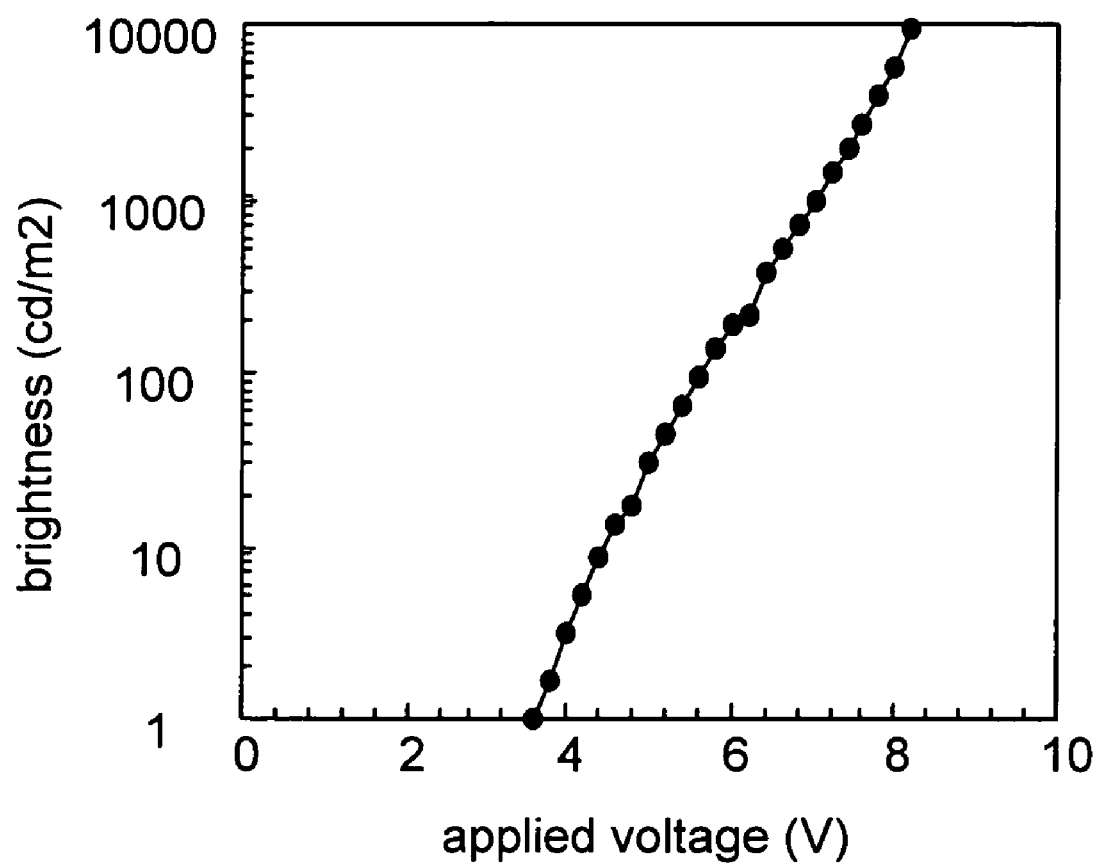
FIG. 12 shows a voltage-brightness curve of an element employing the carbazole derivative according to the invention.

On this film, a film of N-phenyl-3,6-di(N-carbazolyl)carbazole was formed with vacuum evaporation in a thickness of 400 nm, and further a film of Alq, which is an electron transportable material, was formed in 500 nm. On this, a film of CaF$_2$, which is an electron injecting material, was formed in 10 nm, and further a film of an Al electrode was formed in a thickness of 2000 nm. A voltage-brightness curve of the element is shown in FIG. 12. This element started light emission at 3.5 V and gave a brightness of 10000 cd/m$^2$ by applying 8.6 V to exert good properties as an electroluminescence element.

The chromaticity coordinate of the light emission of the element is 0.29 for x and 0.56 for y, which indicates that emission is clearly the green emission from Alq. This means that recombination of carriers occur in the Alq layer. More specifically, a hole injected into the ITO copper phthalocyanine layer is injected into the N-phenyl-3,6-di(N-carbazolyl) carbazole layer and, further, is transported to the Alq. On the other hand, an electron injected from the Al cathode is transported to the Alq layer and recombines with the hole transported from the ITO side to generate an exiton of the Alq. When the exciton of the Alq returns to the ground state, a photon is emitted to result in observation of energy corresponding to the band gap of the Alq as light. Accordingly, it has been clarified that the dendrimer, N-phenyl-3,6-di(N-carbazolyl)carbazole represented in the invention functions as an excellent hole transportable material.

Embodiment 3

In this Embodiment, a portion different in constitution from those in Embodiments 1 and 2, when the carbazole derivative according to the invention is employed as a guest material of the light emitting layer, will be explained by using FIG. 2. Accordingly, in this Embodiment, constitution of the first electrode, the second electrode, the hole injecting layer and the hole transporting layer is the same as those described in Embodiments 1 and 2, and therefore explanation thereof will be omitted.

Figure 2:
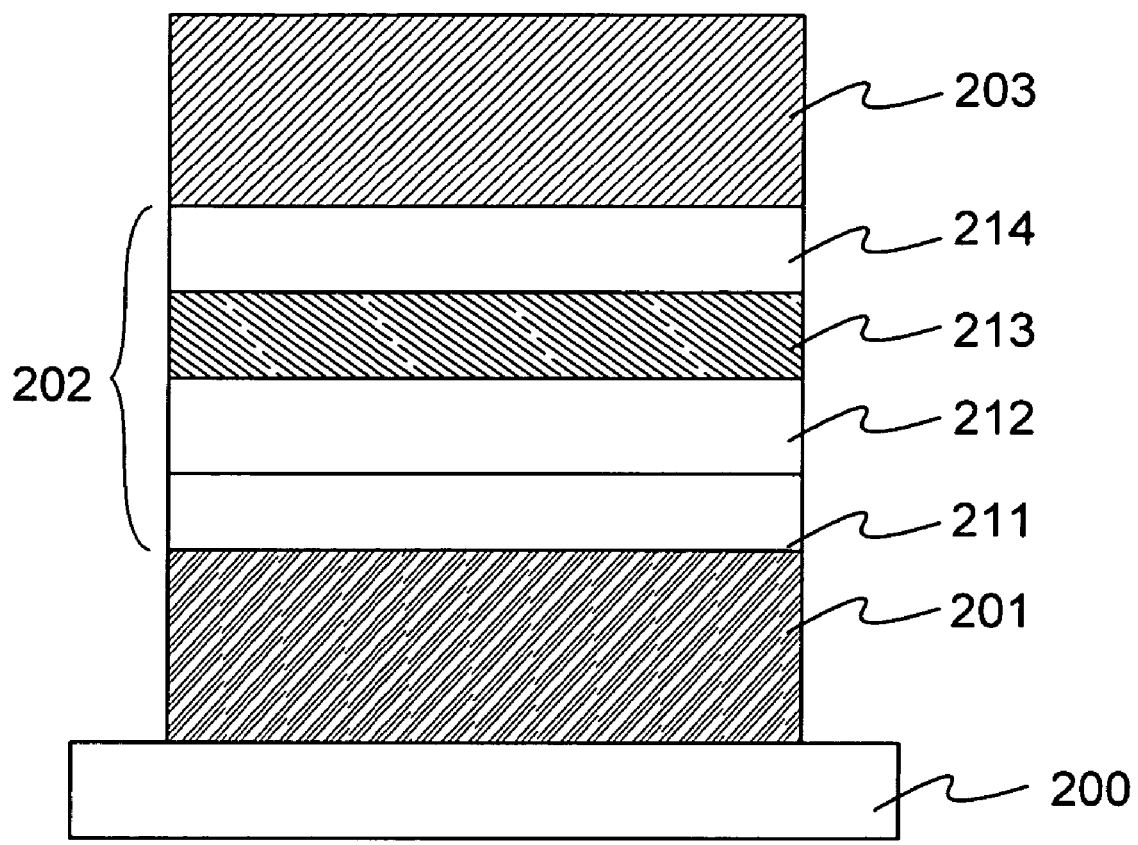
FIG. 2 is a drawing for explaining an element structure of a light emitting element according to the invention.

As shown in FIG. 2, in a layer 202 containing a light emitting material, which is formed over a first electrode 201, a light emitting layer 213 formed adjoining to a hole transporting layer 212 is formed by employing a host material and the guest material being the carbazole derivative according to the invention.

Specifically, TPBI, which is the host material, and $EtCz_2Cz$ (10 wt %) represented by the chemical formula (9), which is the guest material, are employed to form the layer in a thickness of 20 nm with a coevaporation method.

Next, an electron transporting layer 214 is formed. As for the material to form the electron transporting layer 214, publicly known electron transportable materials can be employed and, in the Embodiment, TPBI is employed to form the layer in a thickness of 30 nm with an evaporation method.

In this way, by forming a second electrode 203 over the layer 202 containing the light emitting material formed by laminating the hole injecting layer 211, the hole transporting layer 212, the light emitting layer 213 and the electron transporting layer 214, a light emitting element employing the carbazole derivative according to the invention is formed.

Since the carbazole derivative according to the invention has hole transporting properties as well as light emitting properties, it can be employed, as shown in the Embodiment, as the guest material in the light emitting layer in the layer containing the light emitting material. Further, the carbazole derivative has an excellent heat resistance and is difficult to crystallize when formed into a film, and therefore extension of the lifetime of the light emitting element can be accomplished.

Embodiment 4

In this Embodiment, a portion different in constitution from those in Embodiments 1 to 3, when the carbazole derivative according to the invention is employed for the light emitting layer, will be explained by using FIG. 3. Accordingly, in this Embodiment, constitution of the first electrode, the second electrode and the hole injecting layer is the same as those described in Embodiments 1 and 2, and therefore explanation thereof will be omitted.

Figure 3:
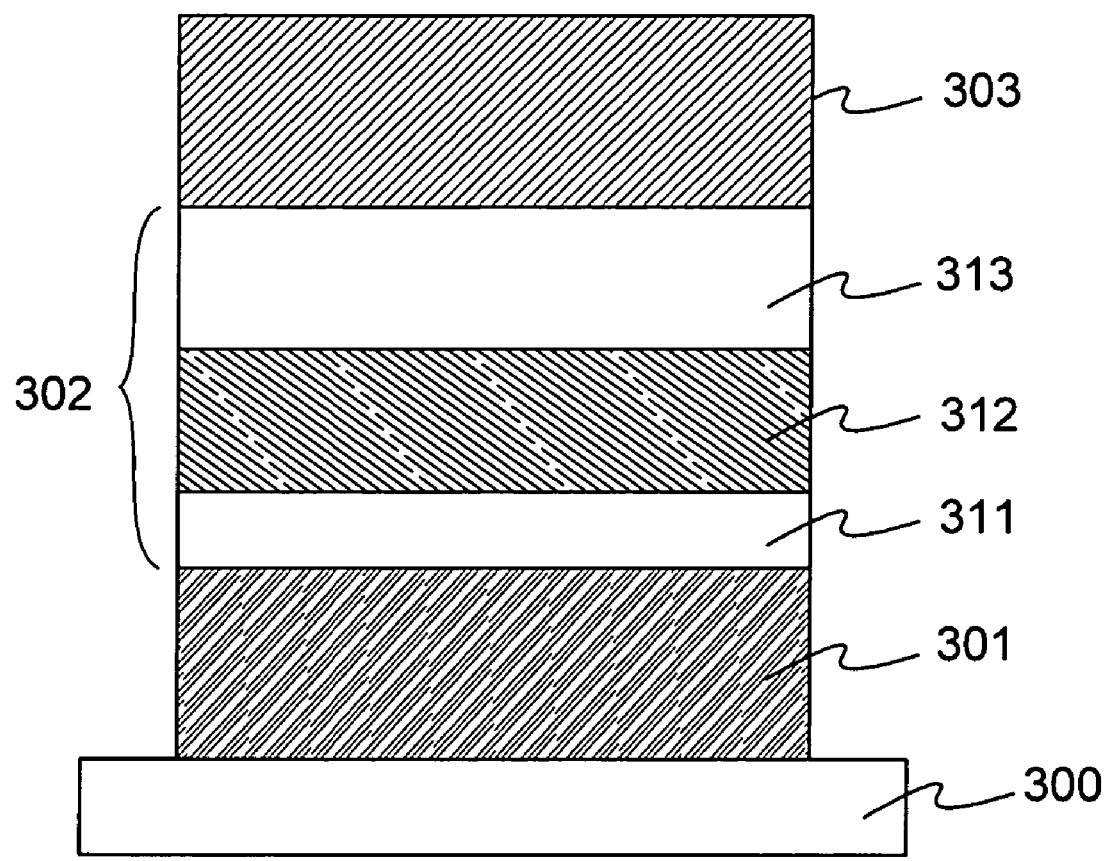
FIG. 3 is a drawing for explaining an element structure of a light emitting element according to the invention.

As shown in FIG. 3, in a layer 302 containing a light emitting material, which is formed over a first electrode 301, a light emitting layer 312 formed adjoining to a hole injecting layer 311 is formed by employing the carbazole derivative according to the invention.

Specifically, it is formed by employing $EtCz_2Cz$ (10 wt %) represented by the chemical formula (9) in a film thickness of 50 nm with an evaporation method.

Next, an electron transporting layer 313 is formed. As for the material to form the electron transporting layer 313, publicly known electron transportable materials can be employed and, in this Embodiment, BCP having electron transport properties as well as hole block properties is employed to form the layer of 50 nm in thickness with an evaporation method.

In this way, by forming a second electrode 303 over the layer 302 containing the light emitting material formed by laminating the hole injecting layer 311, the light emitting layer 312 and the electron transporting layer 313, a light emitting element employing the carbazole derivative according to the invention is formed.

Since the carbazole derivative according to the invention has hole transport properties as well as light emission properties, as shown in the Embodiment, it can be employed individually as the light emitting layer in a layer containing the light emitting material. Further, the carbazole derivative has an excellent heat resistance and is difficult to crystallize when formed into a film, and therefore extension of the lifetime of the light emitting element can be accomplished.

Embodiment 5

In the Embodiment, in the case where the carbazole derivative according to the invention is employed in a portion of a layer containing the light emitting material to produce a light emitting element, a case where constitution is different from those shown in Embodiments 1 to 4 will be explained. Specifically, in the case where the carbazole derivative according to the invention is employed in the hole transporting layer in a layer containing the light emitting material, portions having a constitution different from those in Embodiments 1 to 3 will be explained by using FIG. 4. Accordingly, in the Embodiment, the constitution of the first electrode, the second electrode, the hole injecting layer and the hole transporting layer is the same as those described in Embodiments 1 to 4 and explanation thereof is omitted.

Figure 4:
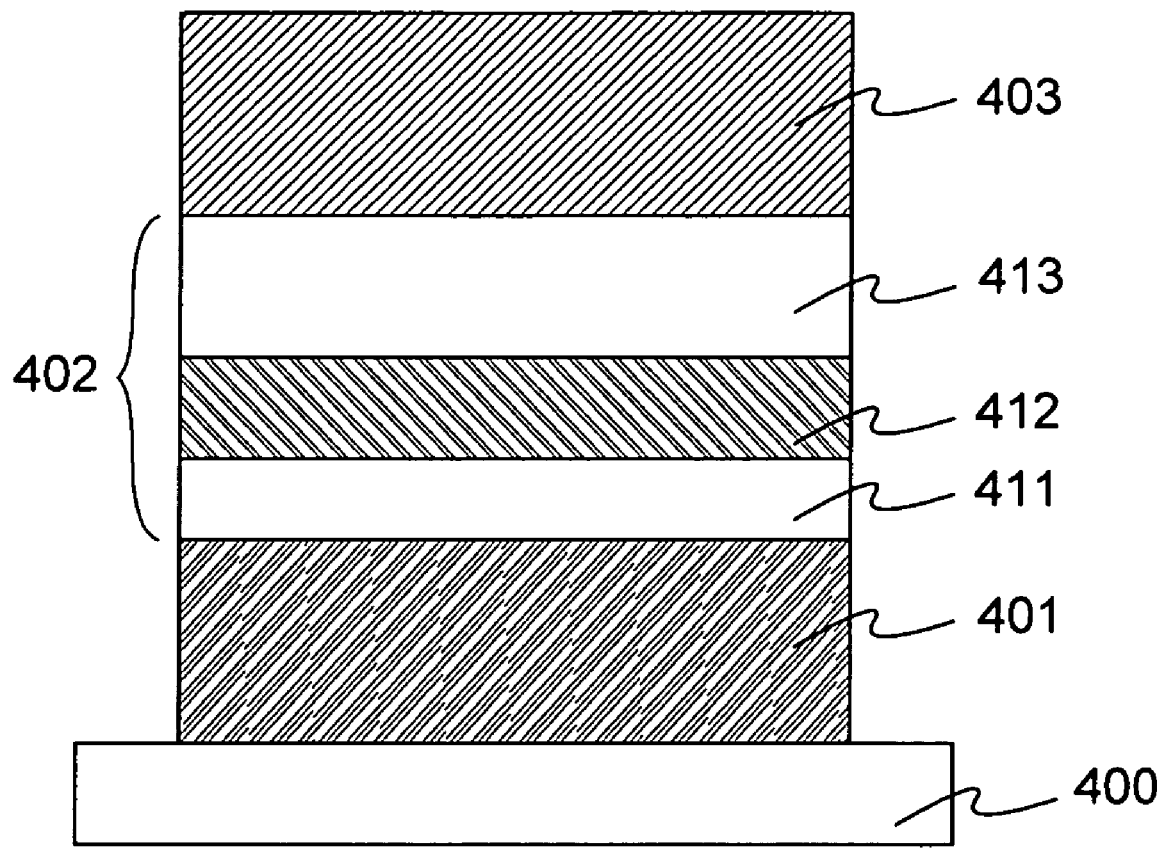
FIG. 4 is a drawing for explaining an element structure of a light emitting element according to the invention.

As shown in FIG. 4, in a layer 402 containing the light emitting material, which is formed over a first electrode 401, a hole transporting layer 412 formed adjoining to a hole injecting layer 411 is formed by employing the carbazole derivative according to the invention.

Specifically, it is formed into a layer of 30 nm in thickness by employing $EtCz_2Cz$ represented by the chemical formula (9) with an evaporation method.

Next, an electron transporting light emitting layer 413 is formed. As for the material to form the electron transporting light emitting layer 413, publicly known materials having electron transporting properties and light emission properties can be employed and, in the Embodiment, $Alq_3$ is employed to form the layer having a thickness of 50 nm with an evaporation method.

In this way, by forming a second electrode 403 over the layer 402 containing the light emitting material, which is formed by laminating the hole injecting layer 411, the hole transporting layer 412 and the electron transporting light emitting layer 413, a light emitting element employing the carbazole derivative according to the invention is formed.

Since the carbazole derivative according to the invention has hole transport properties, as shown in the Embodiment, it can be employed for the hole transporting layer in a layer containing the light emitting material. Further, the carbazole derivative has an excellent heat resistance and is difficult to crystallize when formed into a film, and therefore extension of the lifetime of the light emitting element can be accomplished.

Embodiment 6

In the Embodiment, the case where the carbazole derivative according to the invention is employed as an active layer of a vertical transistor (SIT), which is a kind of an organic semiconductor element, will be explained.

Figure 5:
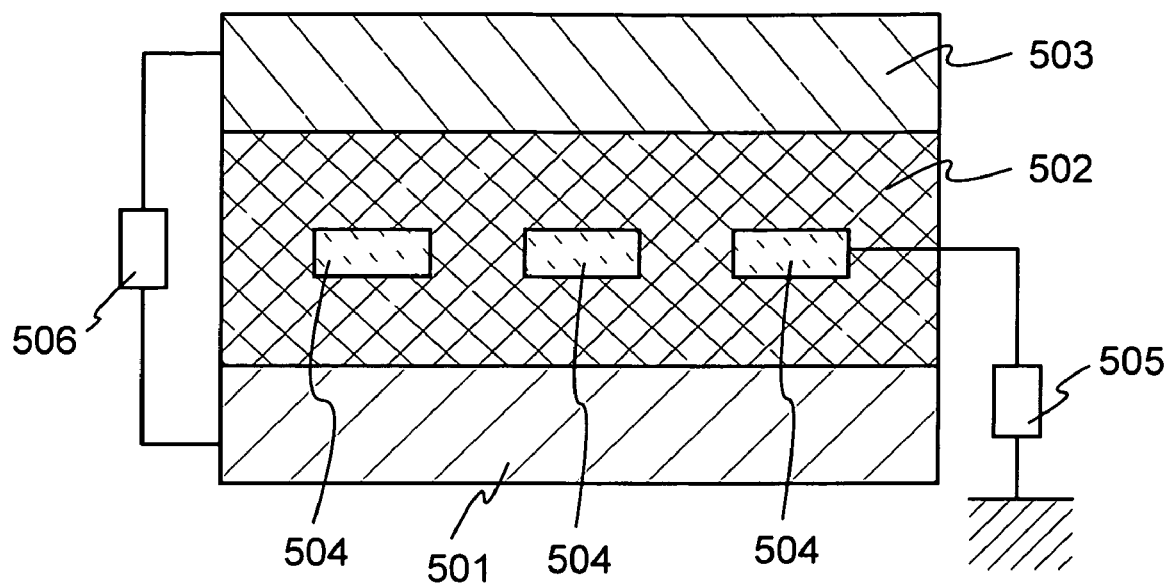
FIG. 5 is a drawing for explaining about an organic semiconductor element applied with the invention.

As for the element construction, as shown in FIG. 5, a construction is applied in which an active layer 502 in a thin film composed of the carbazole derivative according to the invention is sandwiched between a source electrode 501 and a drain electrode 503 and a gate electrode 504 is embedded in the active layer 502. Note that, 505 is a means for applying the gate voltage and 506 is a means for controlling the voltage between the source and drain.

In such element construction, when a voltage is applied between the source and drain in a state of no application of the gate voltage, current like that found in the light emitting element flows (becomes ON state). Then, applying the gate voltage in this state generates a depletion layer near the gate electrode 504 to stop the current (becomes OFF state). According to the aforementioned mechanism, it functions as a transistor.

In the vertical transistor represented in the Embodiment, since flatness of the film forming the active layer tends to influence properties of the element, use of the carbazole derivative according to the invention, which has an excellent heat resistance and can be formed into a film without crystallization, is effective for accomplishing extension of the lifetime of the organic semiconductor element.

Embodiment 7

Figure 6:
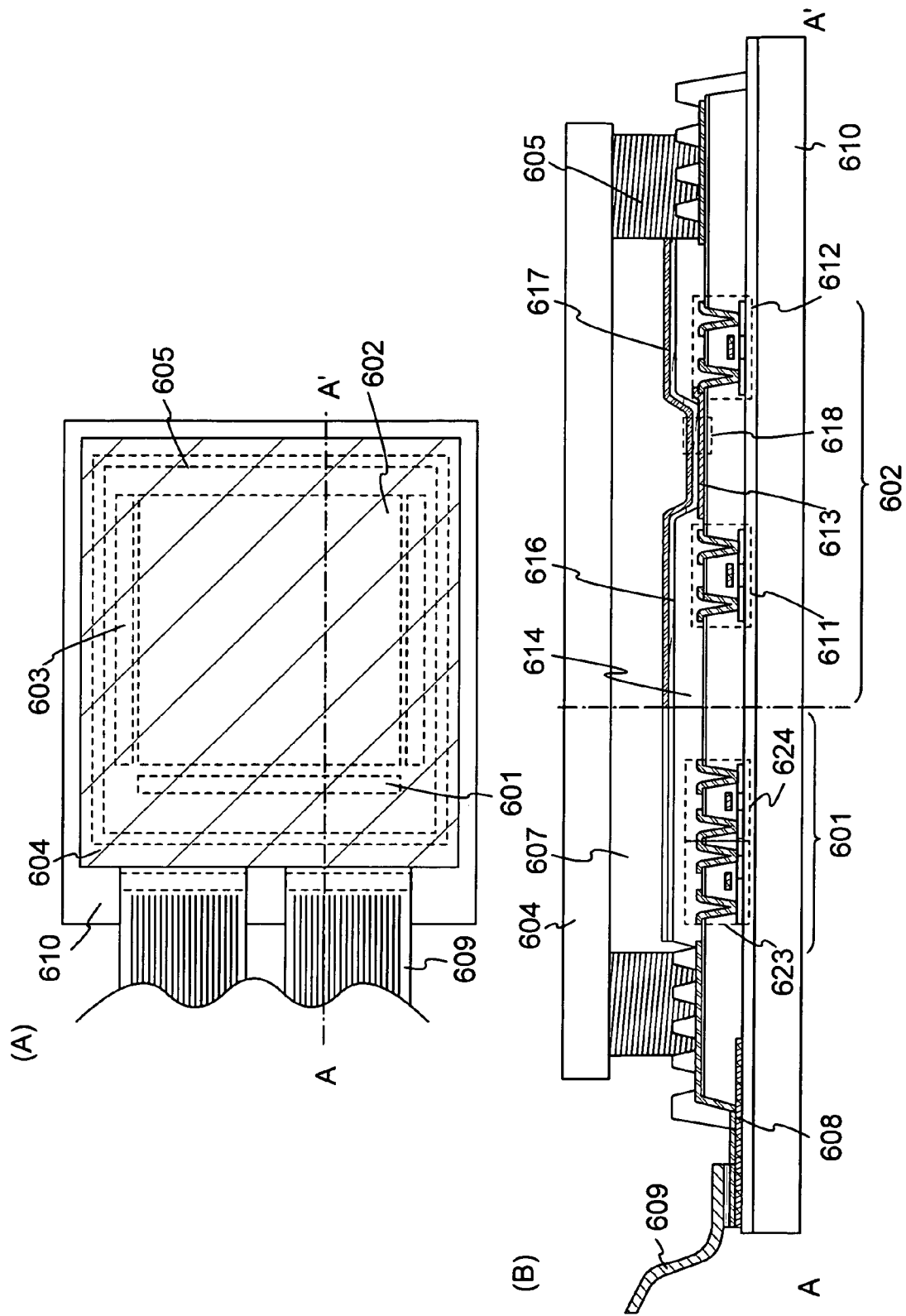
FIG. 6 is a drawing for explaining about a light emitting device.

In the Embodiment, a light emitting device having a light emitting element formed according to the invention in a pixel portion will be explained by using FIG. 6. FIG. 6(A) is a top view illustrating the light emitting device and FIG. 6(B) is a cross-sectional view cutting the FIG. 6(A) along A-A'. 601 represented by a dotted line is a drive circuit portion (source side drive circuit), 602 is a pixel portion and 603 is a drive circuit portion (gate side drive circuit). 604 is a sealing substrate and 605 is a sealing agent. The inside enclosed with the sealing agent 605 is a space 607.

608 is a wiring for transmitting signals input to the source side drive circuit 601 and gate side drive circuit 603. It receives from a FPC (flexible printed circuit) 609, which functions as an external input terminal, a video signal, a clock signal, a start signal, a reset signal and the like. Note that, only the FPC is illustrated here, the FPC may be fitted with a printed-wiring board (PWB). The light emitting device in the specification is intended to include not only a light emitting device main body, but also a state being fitted with a FPC or PWB.

Next, an explanation of a cross-sectional structure will be given by using FIG. 6(B). Over a substrate 610, the drive circuit portion and the pixel portion are formed and, here, the source side drive circuit 601 being the drive circuit portion and the pixel section 602 are illustrated.

The source side drive circuit 601 is composed of a CMOS circuit combining a n-channel type thin film transistor (hereinafter, abbreviate a thin film transistor as TFT) 623 and a p-channel type TFT 624. A TFT forming the drive circuit may be formed with a publicly known CMOS circuit, PMOS circuit or NMOS circuit. Further, in the Embodiment, although a driver-integrated type is illustrated, in which the drive circuit is formed over the substrate, it is not always necessary but the drive circuit may be formed not over the substrate but outside.

The pixel portion 602 is formed by a plurality of pixels including a TFT 611 for switching, a TFT 612 for electric current control and a first electrode 613 connected electrically to the drain thereof. An insulator 614 is formed covering the edge portion of the first electrode 613, which is formed here by employing a positive type photosensitive acrylic resin film.

Further, it is designed such that a curved surface having a curvature is formed at an upper end portion or a lower end portion of the insulator 614 in order to improve film formability. For example, in the case where a positive type photosensitive acrylic is employed for the material of the insulator 614, it is preferable that only the upper end portion of the insulator 614 is allowed to have a curved surface having a curvature radius (0.2 μm to 3 μm). Here, as the insulator 614, either a negative type which becomes insoluble in an etchant by a photosensitive light or a positive type which becomes soluble in an etchant by a light may be employed.

Over the first electrode 613, a layer 616 containing a light emitting material and a second electrode 617 are formed respectively. Here, as for the material of the first electrode 613 functioning as an anode, use of a material having a large work function is desirable. For example, in addition to single layer films such as an ITO (indium tin oxide) film, an indium zinc oxide (IZO) film, a titanium nitride film, a chromium film, a tungsten film, a Zn film and a Pt film, a laminate of titanium nitride film and a film containing aluminum as the main component, and a three-layer construction of a titanium nitride film, a film containing aluminum as the main component and a titanium nitride film, and the like can be employed. A laminate structure results in a low resistance as a wiring and good ohmic contact, and further allows to function as an anode.

The layer 616 containing the light emitting material is formed by an evaporation method using an evaporation mask or an ink jet method. The layer 616 containing the light emitting material contains the carbazole derivative according to the invention. Materials used in combination with these carbazole derivatives may be a low molecular weight material, a medium molecular weight material (including oligomer and dendrimer) or a high molecule weight material. As for materials for use in a layer containing the light emitting material, usually organic compounds are often employed in a single layer or a laminated layer but, in the invention, a constitution in which an inorganic compound is employed in a part of a film composed of an organic compound is intended to be included.

As for the material for use in the second electrode (cathode) 617 formed over the layer 616 containing the light emitting material, a material having a small work function (Al, Ag, Li, Ca, or an alloy thereof such as MgAg, MgIn, AlLi, $CaF_2$ or CaN) can be employed. Note that, in the case where the light generated in the layer 616 containing the light emitting material is allowed to transmit the second electrode 617, a laminate of a metal thin film having a small thickness and a transparent conductive film (such as an ITO (indium oxide-tin oxide alloy), an indium oxide-zinc oxide alloy (In$_2$O$_3$—ZnO), or a zinc oxide(ZnO)) can be employed as the second electrode (cathode) 617.

Further, by pasting the sealing substrate 604 to the element substrate 610 with the sealing agent 605, such construction is introduced that a light emitting element 618 is provided in the space 607 enclosed by the element substrate 610, sealing substrate 604 and the sealing agent 605. Note that, in addition to the case where the space 607 is filled with an inert gas (such as nitrogen or argon), the constitution in which it is filled with the sealing agent 605 is also intended to be included.

As for the sealing agent 605, use of an epoxy-series resin is preferable. These materials are desired to be a material that does not allow moisture and oxygen to permeate as far as possible. As for the material for use in the sealing substrate 604, in addition to a glass substrate and a quartz substrate, a plastic substrate composed of FRP (Fiberglass-Reinforced Plastics), PVF (polyvinyl fluoride), mylar, polyester, acrylic or the like can be employed.

As described above, a light emitting device having the light emitting element formed according to the invention can be obtained.

Note that, the light emitting device represented in the Embodiment may be carried out by combining freely the constitutions of the light emitting element represented in Embodiments 1 to 4.

Embodiment 8

In this Embodiment, various electronic devices including light emitting devices formed in the Embodiment 7, for example, in a part thereof will be explained.

Figure 7:
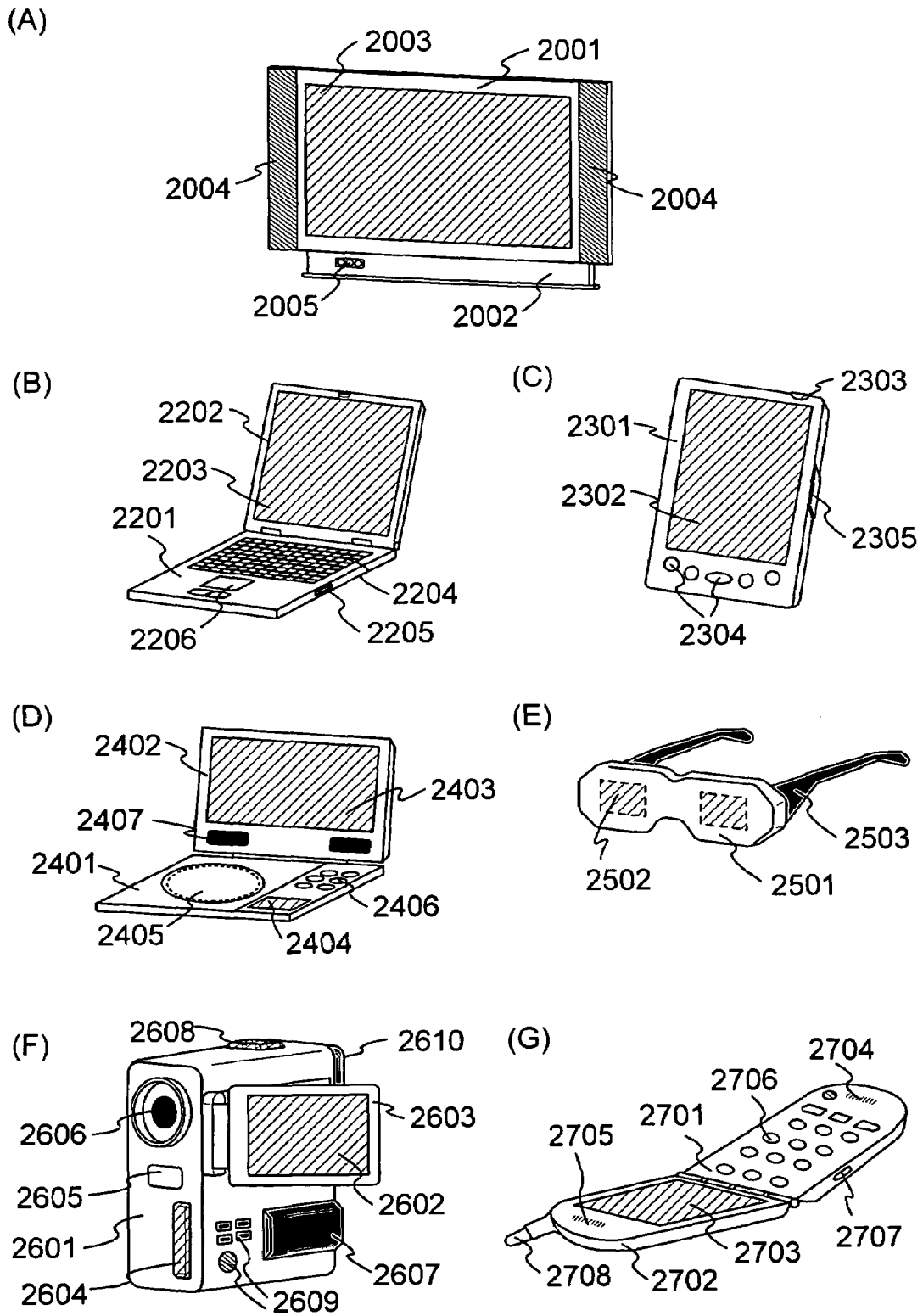
FIG. 7 is a drawing for explaining about an electronic device.

Examples of such electronic devices manufactured by using a light emitting device formed using the invention are given: a video camera, a digital camera, a goggle-type display (head mounted display), a navigation system, a sound reproduction device (a car audio, an audio compo and the like), a laptop personal computer, a game machine, a portable information terminal (a mobile computer, a cellular phone, a portable game machine, an electronic book, or the like), an image reproduction device including a recording medium (more specifically, a device which reproduces a recording medium such as a digital video disc (DVD), and so forth, and includes a display device for displaying the reproduced image), or the like. FIG. 7 shows specific examples of these electronic devices.

FIG. 7(A) shows a display device composed of a housing 2001, a support 2002, a display portion 2003, speaker portions 2004, a video input terminal 2005, and the like. The display device is fabricated by using a light emitting device formed according to the invention for the display portion 2003. It includes display devices for all information such as for a personal computer, TV broadcast reception, advertisement, and the like.

FIG. 7(B) shows a laptop personal computer composed of a main body 2201, a housing 2202, a display portion 2203, a keyboard 2204, an external connection port 2205, a pointing mouse 2206, and the like. It is fabricated by using a light emitting device formed according to the invention for the display portion 2203.

FIG. 7(C) shows a mobile computer composed of a main body 2301, a display portion 2302, a switch 2303, operation keys 2304, an infrared port 2305, and the like. It is fabricated by using a light emitting device formed according to the invention for the display portion 2302.

FIG. 7(D) shows a portable image reproduction device including a recording medium (specifically, a DVD reproduction device) composed of a main body 2401, a housing 2402, a display portion A 2403, a display portion B 2404, a recording medium reading portion 2405, an operation key 2406, a speaker portion 2407, and the like. The recording medium given here indicates DVD and the like. The display portion A 2403 is mainly used for displaying image information, while the display portion B 2404 is mainly used for displaying character information. It is fabricated by using a light emitting device formed according to the invention for the display portion A 2403 and the display portion B 2404. The image reproduction device including a recording medium further includes a domestic game machine, or the like.

FIG. 7(E) shows a goggle type display (head mounted display) composed of a main body 2501, a display portion 2502, and an arm portion 2503. It is fabricated by using a light emitting device formed according to the invention for the display portion 2502.

FIG. 7(F) shows a video camera composed of a main body 2601, a display portion 2602, a housing 2603, an external connecting port 2604, a remote control receiving portion 2605, an image receiving portion 2606, a battery 2607, a sound input portion 2608, operation keys 2609, an eye piece potion 2610, and the like. It is fabricated by using a light emitting device formed according to the invention for the display portion 2602.

FIG. 7(G) shows a cellular phone composed of a main body 2701, a housing 2702, a display portion 2703, a sound input portion 2704, a sound output portion 2705, an operation key 2706, an external connecting port 2707, an antenna 2708, and the like. It is fabricated by using a light emitting device formed according to the invention for the display portion 2703.

As described above, the applicable range of a light emitting device formed according to the invention is extremely large and a light emitting element used for the light emitting device is formed by using a carbozole derivative according to the invention and therefore have a characteristic of a low drive voltage and a long lifetime. Accordingly, by applying the light emitting devices to electronic devices in every field, they can accomplish the reduction of the power consumption and the extension of the lifetime.

INDUSTRIAL APPLICABILITY

By carrying out the invention, a carbazole derivative, which has an excellent heat resistance and a hole transport properties and can be formed into a film without crystallization, can be obtained. Further, by producing an organic semiconductor element, a light emitting element and an electronic device by employing the carbazole derivative, it is possible to provide the organic semiconductor element, the light emitting element and the electronic device having a low drive voltage and a long lifetime. Furthermore, by forming a light emitting device by employing the light emitting element, it is possible to provide the light emitting device with a low power consumption and a long lifetime.

What is claimed is:

1. A carbazole derivative represented by general formula (1):

(1)

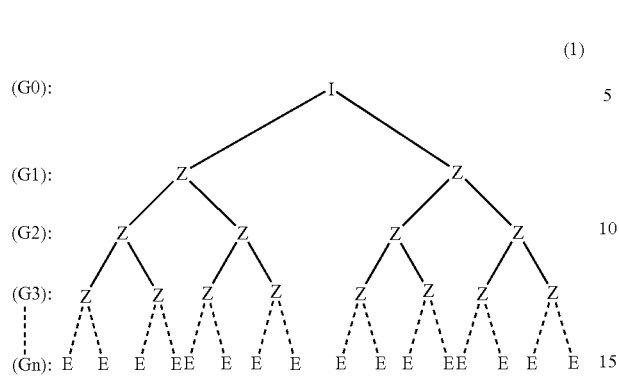

in the formula, I represents a core carbazole ($G_0$) illustrated by general formula (2), Z represents an internally branched carbazole ($G_1$ to $G_{n-1}$) illustrated by general formula (3), E represents an end carbazole ($G_n$) illustrated by general formula (4), n represents an integer showing generation number of dendrimer, $X_1$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue, $C_A$ and $C_B$ in ($G_{(n-m)-1}$) (provided, n-m≧1) make a covalent bond with $N_A$ in ($G_{(n-m)}$), and each of $R_1$ to $R_8$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10) or a substituted or unsubstituted heterocyclic residue

I:

(2)

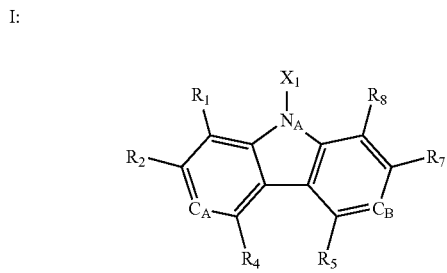

Z:

(3)

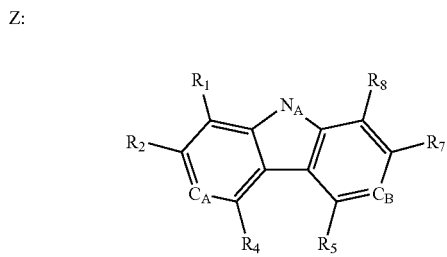

E:

(4)

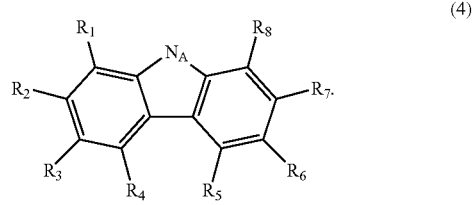

2. A carbazole derivative represented by general formula (5):

in the formula 3≦k<8 and $X_2$ represents an alkyl group (provided, carbon number ranges from 1 to 20), a haloalkyl group (provided, carbon number ranges from 1 to 20), an alkoxy group (provided, carbon number ranges from 1 to 20), or a substituted or unsubstituted aryl group (5)

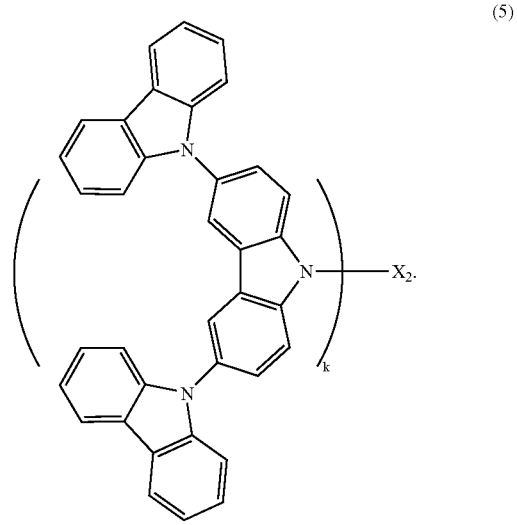

3. A carbazole derivative represented by general formula (6):

(6)

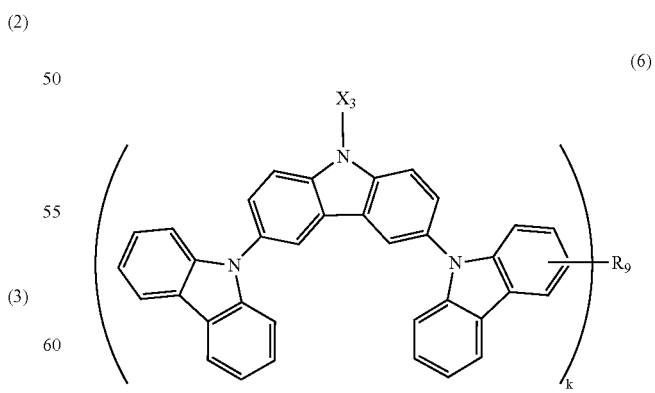

in the formula, 1<k<8, each of $R_9$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10), a substituted or unsubstituted aryl group or a substituted or unsubstituted heterocyclic residue, and $X_3$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue.

4. A carbazole derivative represented by general formula (7):

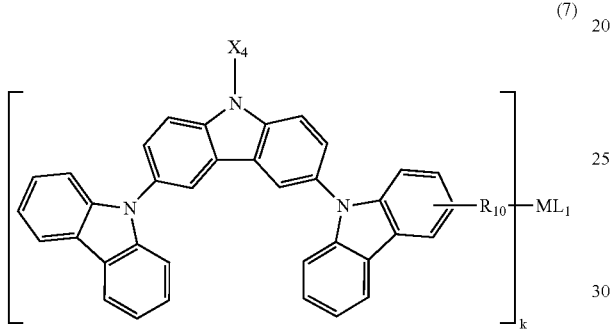

(7)

in the formula, 1<k<8, 0<l<8, each of $R_{10}$ represents independently hydrogen, halogen, a cynano group, an alkyl group (provided, carbon number ranges from 1 to 20), an acyl group (provided, carbon number ranges from 1 to 20), a haloalkyl group (provided, carbon number ranges from 1 to 20), a dialkylamino group (provided, carbon number ranges from 1 to 20), a diarylamino group (provided, carbon number ranges from 1 to 20), an alkoxy group (provided, carbon number ranges from 1 to 10), a substituted or unsubstituted aryl group or a substituted or unsubstituted heterocyclic residue, M represents a metal ion of zero to hexavalent, L represents an aryl group, a dialkylphosphino group or a diarylphosphino group, and $X_4$ represents hydrogen, halogen, a cynano group, an alkyl group (provided, carbon number ranges from 1 to 20), a haloalkyl group (provided, carbon number ranges from 1 to 20), an alkoxy group (provided, carbon number ranges from 1 to 20), a substituted or unsubstituted aryl group or a substituted or unsubstituted heterocyclic residue.

5. The carbazole derivative according to claim 3, wherein $R_9$ in the formula (6) is any one of heterocyclic residues represented by the following structural formulas, and M in the following structural formulas is Pt or Cu:

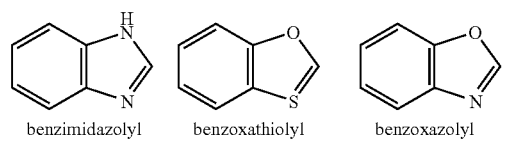

benzimidazolyl    benzoxathiolyl    benzoxazolyl

-continued

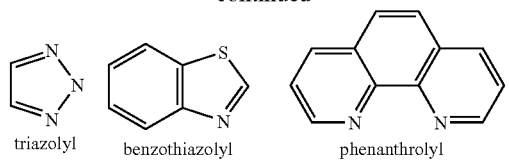

triazolyl    benzothiazolyl    phenanthrolyl

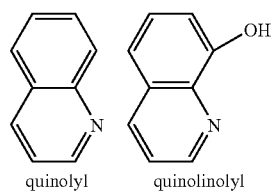

quinolyl    quinolinolyl

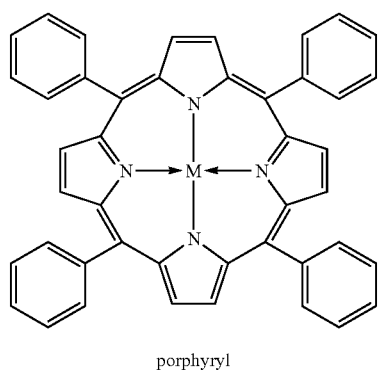

porphyryl

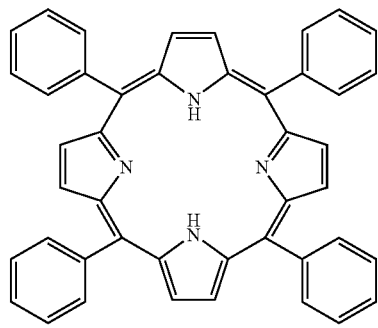

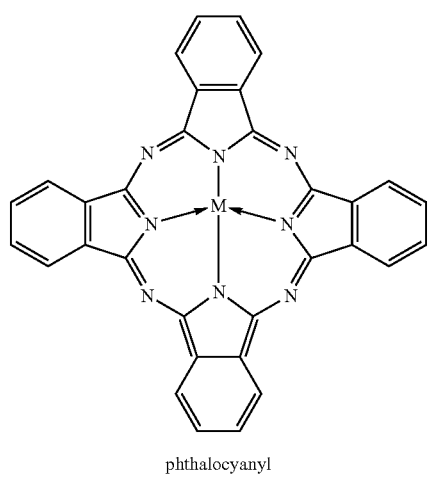

phthalocyanyl

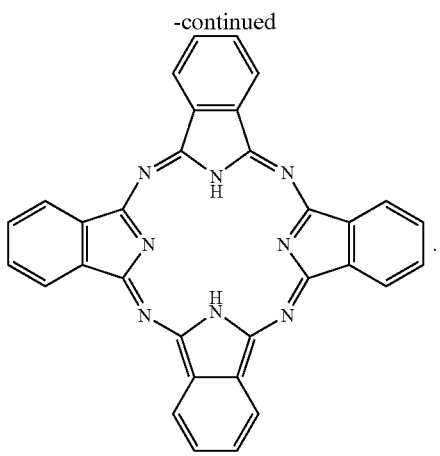

6. An organic semiconductor element employing the carbazole derivative according to claim 3.

7. A light emitting element employing the carbazole derivative according to claim 3.

8. A light emitting element employing the carbazole derivative according to claim 3 as a light emitting material.

9. A light emitting element having a light emitting layer containing the carbazole derivative according to claim 3 and a guest material.

10. A light emitting element having a light emitting layer containing the carbazole derivative according to claim 3 and a host material.

11. A light emitting element employing the carbazole derivative according to claim 3 as a hole transportable material.

12. An electronic device having a light emitting element containing the carbazole derivative according to claim 3, wherein the electronic device is selected from the group consisting of a display device, a digital still camera, a personal computer, a mobile computer, an image reproduction device, a goggle type display, a video camera and a cellular phone.

13. An electronic device having an organic semiconductor element containing the carbazole derivative according to claim 3, wherein the electronic device is selected from the group consisting of a display device, a digital still camera, a personal computer, a mobile computer, an image reproduction device, a goggles-type display, a video camera and a cellular phone.

14. A carbazole derivative represented by general formula (5):

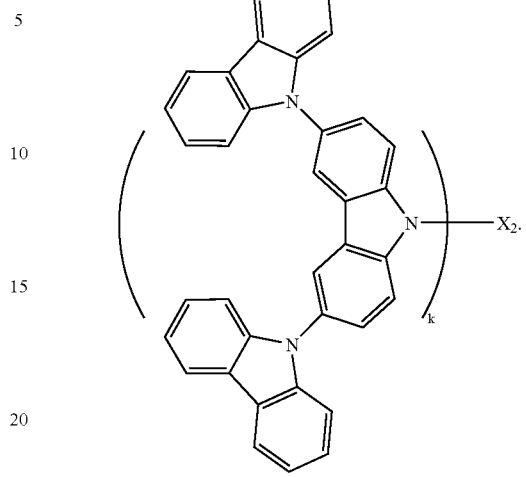

in the formula, k=2, and $X_2$ represents an alkyl group (provided, carbon number ranges from 1 to 5), a haloalkyl group (provided, carbon number ranges from 3 to 7), or an alkoxy group (provided, carbon number ranges from 1 to 20

15. An organic semiconductor element employing the carbazole derivative according to claim 14.

16. A light emitting element employing the carbazole derivative according to claim 14.

17. A light emitting element employing the carbazole derivative according to claim 14 as a light emitting material.

18. A light emitting element having a light emitting layer containing the carbazole derivative according to claim 14 and a guest material.

19. A light emitting element having a light emitting layer containing the carbazole derivative according to claim 14 and a host material.

20. A light emitting element employing the carbazole derivative according to claim 14 as a hole transportable material.

21. An electronic device having a light emitting element containing the carbazole derivative according to claim 14, wherein the electronic device is selected from the group consisting of a display device, a digital still camera, a personal computer, a mobile computer, an image reproduction device, a goggle type display, a video camera and a cellular phone.

22. An electronic device having an organic semiconductor element containing the carbazole derivative according to claim 14, wherein the electronic device is selected from the group consisting of a display device, a digital still camera, a personal computer, a mobile computer, an image reproduction device, a goggles-type display, a video camera and a cellular phone.

* * * * *